(12) United States Patent
Asada et al.

(10) Patent No.: US 8,493,558 B2
(45) Date of Patent: Jul. 23, 2013

(54) SURFACE INSPECTION APPARATUS

(75) Inventors: Yasunori Asada, Okazaki (JP); Norio Miyazato, Sagamihara (JP); Eiji Yamazaki, Kazo (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 780 days.

(21) Appl. No.: 12/575,543

(22) Filed: Oct. 8, 2009

(65) Prior Publication Data

US 2010/0091272 A1 Apr. 15, 2010

(30) Foreign Application Priority Data

Oct. 10, 2008 (JP) .................................. 2008-264308
Mar. 31, 2009 (JP) .................................. 2009-087972

(51) Int. Cl.
*G01N 21/00* (2006.01)
*G01B 11/24* (2006.01)
*G06K 9/00* (2006.01)

(52) U.S. Cl.
USPC ............... 356/237.2; 356/237.1; 356/237.3; 356/601; 382/141; 382/152

(58) Field of Classification Search
None
See application file for complete search history.

(56) References Cited

U.S. PATENT DOCUMENTS

| | | | | |
|---|---|---|---|---|
| 4,852,985 A | * | 8/1989 | Fujihara et al. | 359/387 |
| 5,039,868 A | * | 8/1991 | Kobayashi et al. | 250/559.08 |
| 5,304,813 A | * | 4/1994 | De Man | 250/556 |
| 5,498,879 A | * | 3/1996 | De Man | 250/556 |
| 6,064,478 A | * | 5/2000 | Paul et al. | 356/237.1 |
| 6,122,042 A | * | 9/2000 | Wunderman et al. | 356/73 |
| 6,239,870 B1 | * | 5/2001 | Heuft | 356/239.5 |
| 6,690,466 B2 | * | 2/2004 | Miller et al. | 356/326 |
| 6,947,151 B2 | * | 9/2005 | Fujii et al. | 356/612 |
| 6,983,066 B2 | * | 1/2006 | Mahon et al. | 382/141 |
| 7,126,699 B1 | * | 10/2006 | Wihl et al. | 356/625 |
| 7,193,697 B2 | * | 3/2007 | Sung et al. | 356/237.1 |

(Continued)

FOREIGN PATENT DOCUMENTS

| | | | |
|---|---|---|---|
| CN | 101221122 A | * | 7/2008 |
| JP | 62-63842 | | 3/1987 |

(Continued)

OTHER PUBLICATIONS

Notification of Reason(s) for Refusal for JP 2009-087972 issued Jul. 27, 2010.

(Continued)

*Primary Examiner* — Gordon Stock, Jr.
(74) *Attorney, Agent, or Firm* — Finnegan, Henderson, Farabow, Garrett & Dunner, LLP

(57) ABSTRACT

A surface inspection apparatus includes an irradiating unit that has a plurality of light sources that respectively emit a plurality of illumination light beams having different wavelength ranges, and irradiates an inspection surface as a surface of a body to be inspected with the illumination light beams, in a condition where the light sources are located adjacent to each other and arranged in a given order along the inspection surface, an imaging unit that images reflected light when the illumination light beams are reflected by the inspection surface, so as to obtain a plurality of items of image data corresponding to the respective wavelength ranges, and a control unit that detects a detection object on the inspection surface, based on the items of image data corresponding to the respective wavelength ranges which are obtained by the imaging unit.

2 Claims, 24 Drawing Sheets

U.S. PATENT DOCUMENTS

| | | | |
|---|---|---|---|
| 7,446,864 B2 * | 11/2008 | Okabe et al. | 356/237.1 |
| 7,505,149 B2 * | 3/2009 | Ishiba et al. | 356/612 |
| 7,969,565 B2 * | 6/2011 | Stober | 356/237.2 |
| 8,118,217 B1 * | 2/2012 | Ma et al. | 235/379 |
| 2004/0061856 A1 * | 4/2004 | Clark et al. | 356/334 |
| 2006/0000989 A1 * | 1/2006 | Kuriyama et al. | 250/559.34 |
| 2006/0228017 A1 * | 10/2006 | Kuramasu et al. | 382/141 |
| 2006/0239547 A1 * | 10/2006 | Robinson et al. | 382/162 |
| 2008/0062416 A1 * | 3/2008 | Colle | 356/240.1 |
| 2008/0186481 A1 * | 8/2008 | Chen | 356/237.1 |
| 2009/0073716 A1 * | 3/2009 | Ikeda et al. | 362/558 |
| 2009/0236542 A1 * | 9/2009 | Wallis | 250/459.1 |

FOREIGN PATENT DOCUMENTS

| | | | |
|---|---|---|---|
| JP | 63-167208 | | 7/1988 |
| JP | 01113639 A | * | 5/1989 |
| JP | 1-250810 | | 10/1989 |
| JP | 2-78937 | | 3/1990 |
| JP | 4-106461 | | 4/1992 |
| JP | 04113260 A | * | 4/1992 |
| JP | 5-60041 | | 9/1993 |
| JP | 6-201342 | | 7/1994 |
| JP | 9-79988 | | 3/1997 |
| JP | 3059108 | | 3/1999 |
| JP | 11-237210 | | 8/1999 |
| JP | 2003-28805 | | 1/2003 |
| JP | 2003121371 A | * | 4/2003 |
| JP | 2003-270173 | | 9/2003 |
| JP | 2003-329612 | | 11/2003 |
| JP | 2004-85205 | | 3/2004 |
| JP | 2006-98093 | | 4/2006 |
| JP | 2006-250942 | | 9/2006 |
| JP | 2006-292412 | | 10/2006 |
| JP | 2009031228 A | * | 2/2009 |

OTHER PUBLICATIONS

Notification of Reason(s) for Refusal for Japanese Appl. No. 2009-087972 dated Dec. 7, 2010.

* cited by examiner

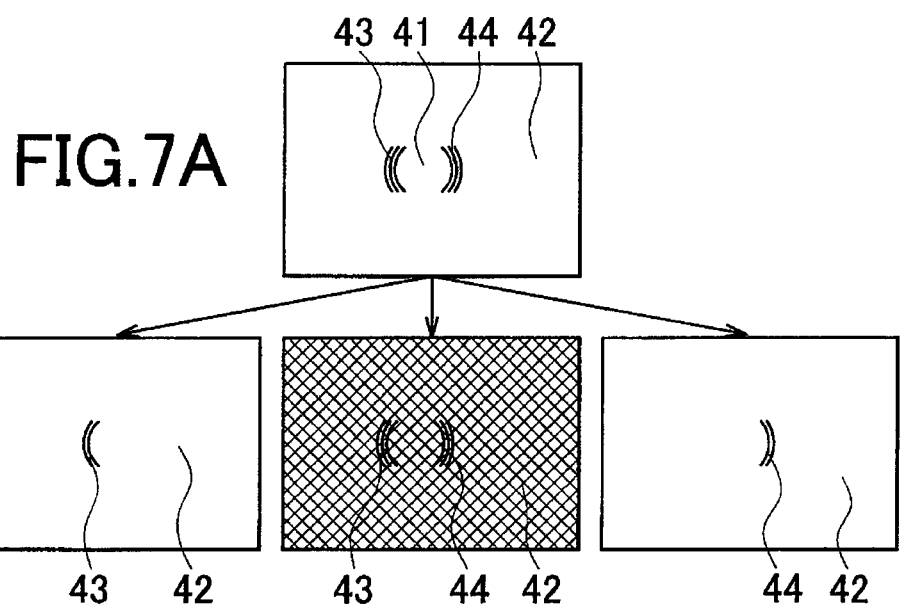

F I G . 11
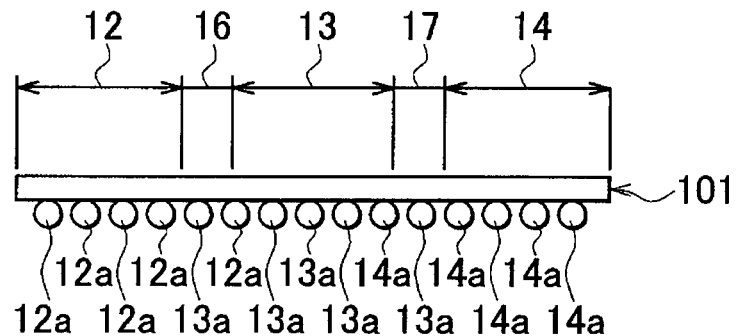
F I G . 12
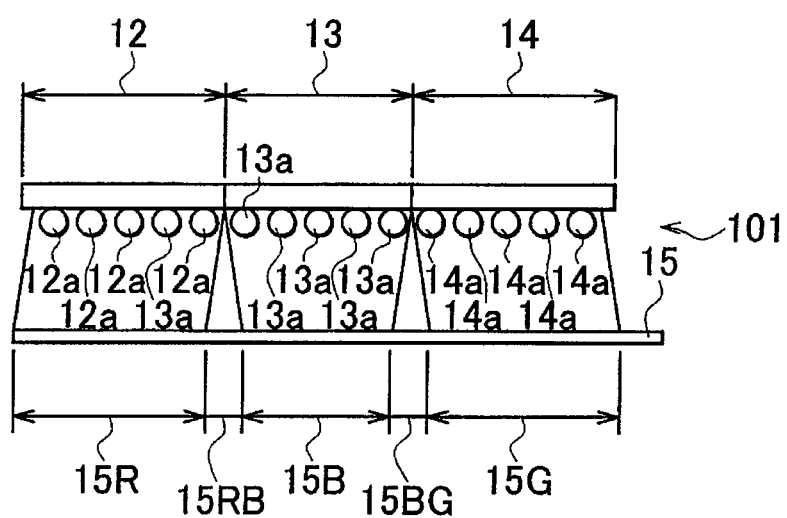

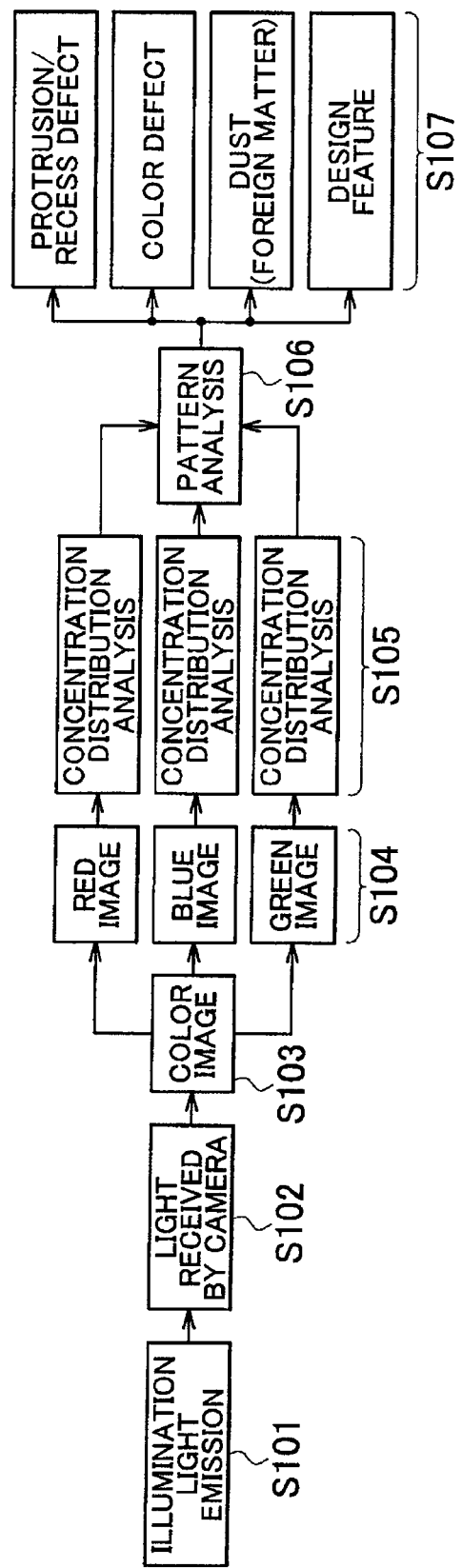

FIG. 14

|  |  | RED (BLUE,GREEN) | BLUE (GREEN,RED) | GREEN (RED, BLUE) |
|---|---|---|---|---|
| PROTRUSION/ RECESS DEFECT | SPECULAR REFLECTION AMOUNT | LARGE | SMALL | LARGE |
|  | DIFFUSE REFLECTION AMOUNT | EXTREMELY SMALL | EXTREMELY SMALL | EXTREMELY SMALL |
| DARK-COLOR DEFECT (DARK-COLOR DEFECT ON LIGHT -COLOR PANEL) | SPECULAR REFLECTION AMOUNT | SMALL | LARGE | SMALL |
|  | DIFFUSE REFLECTION AMOUNT | EXTREMELY SMALL | EXTREMELY SMALL | EXTREMELY SMALL |
| LIGHT-COLOR DEFECT (LIGHT-COLOR DEFECT ON DARK -COLOR PANEL) | SPECULAR REFLECTION AMOUNT | SMALL | LARGE | SMALL |
|  | DIFFUSE REFLECTION AMOUNT | MEDIUM | MEDIUM | MEDIUM |
| DUST (FOREIGN MATTER) | SPECULAR REFLECTION AMOUNT | SMALL | SMALL | SMALL |
|  | DIFFUSE REFLECTION AMOUNT | SMALL | EXTREMELY SMALL | EXTREMELY SMALL |
| DESIGN FEATURE | SPECULAR REFLECTION AMOUNT | EXTREMELY SMALL | EXTREMELY SMALL | EXTREMELY SMALL |
|  | DIFFUSE REFLECTION AMOUNT | EXTREMELY SMALL | EXTREMELY SMALL | EXTREMELY SMALL |

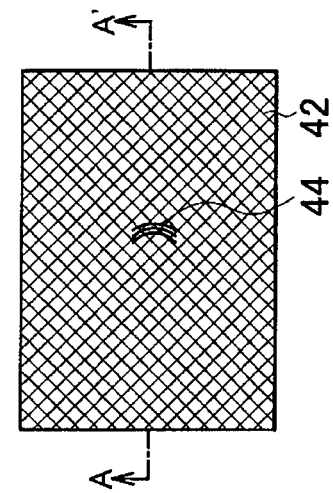
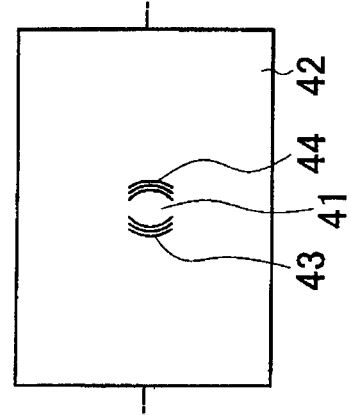
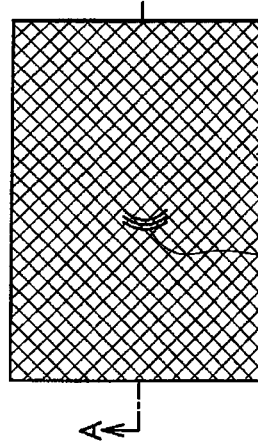
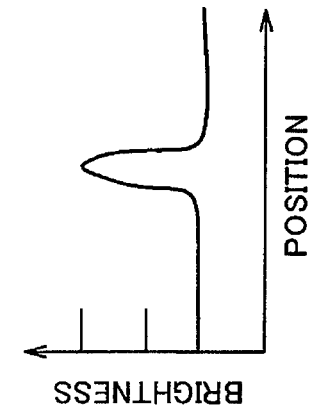
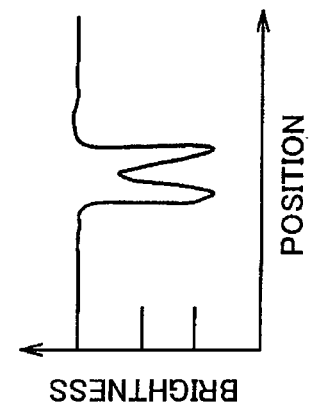
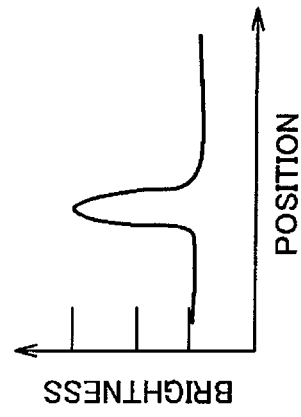

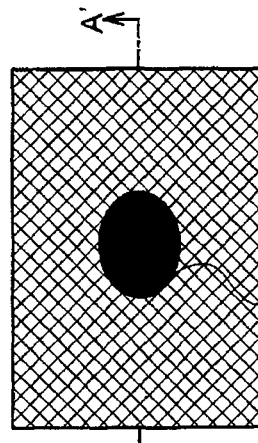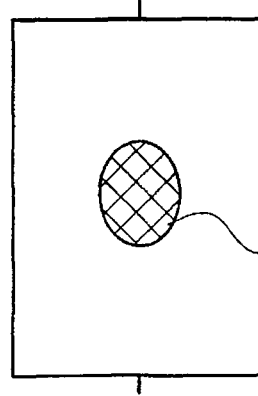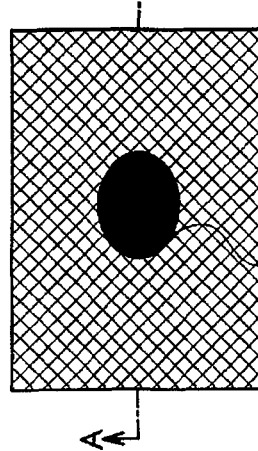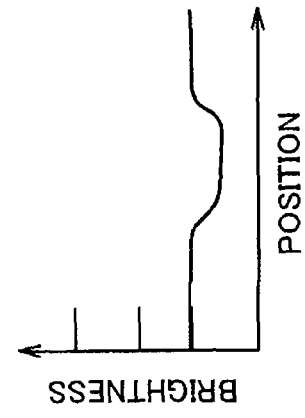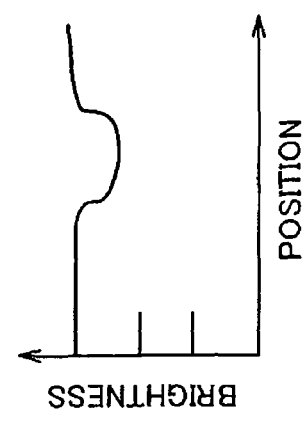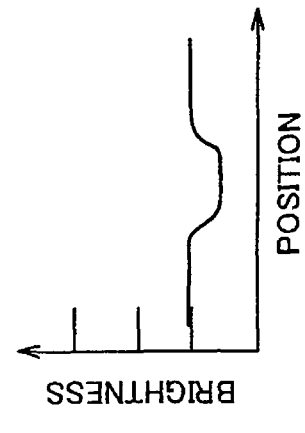

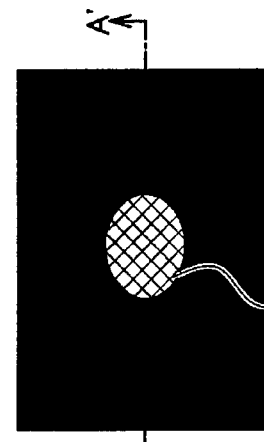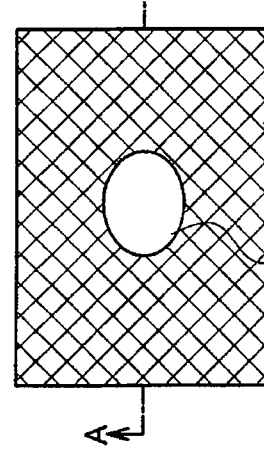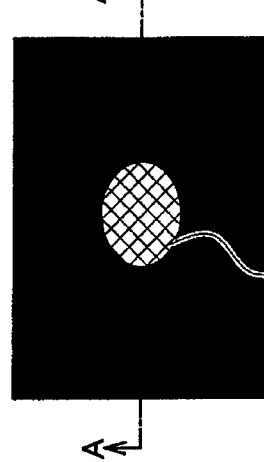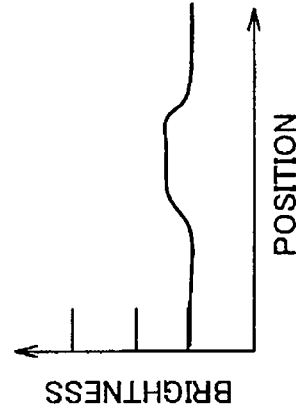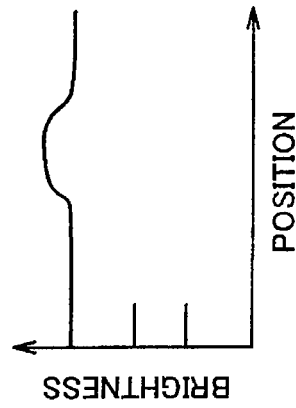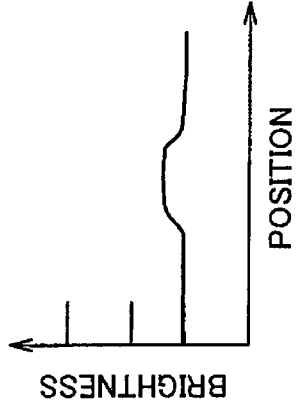

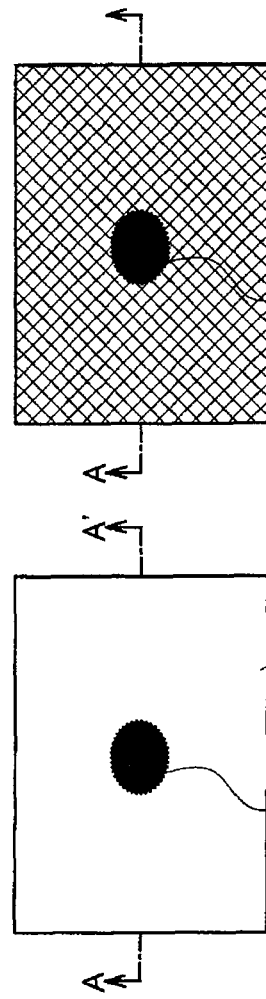
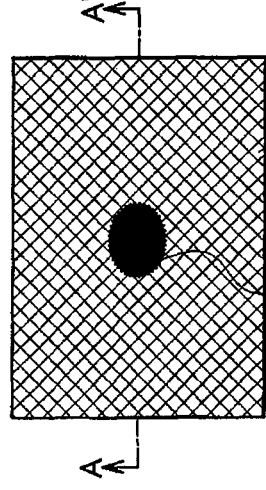

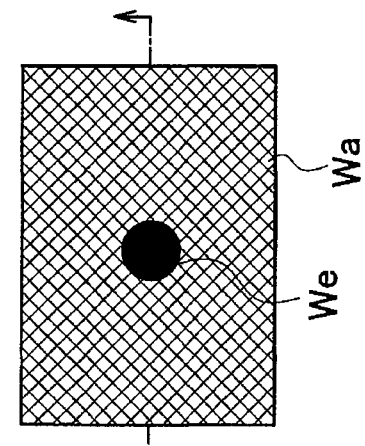
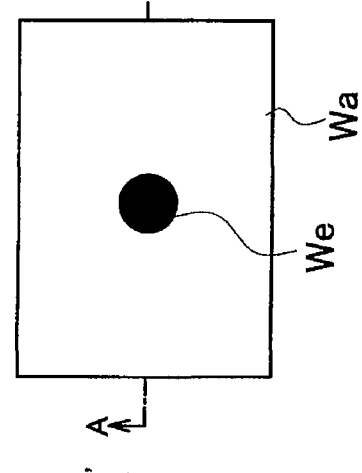
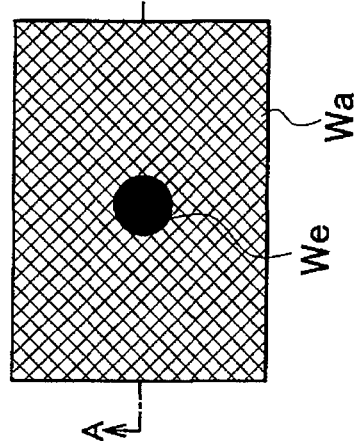
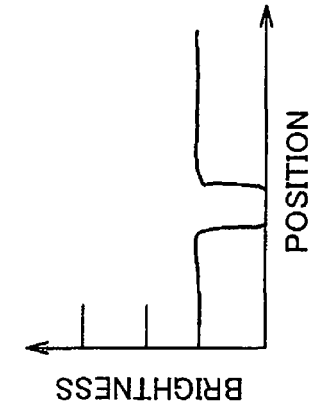
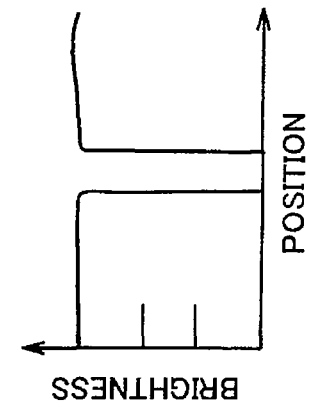
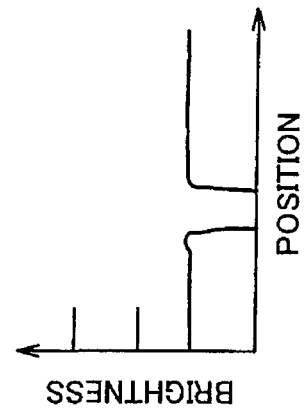

SURFACE INSPECTION APPARATUS

INCORPORATION BY REFERENCE

The disclosures of Japanese Patent Application No. 2008-264308 filed on Oct. 10, 2008 and Japanese Patent Application No. 2009-087972 filed on Mar. 31, 2009 including the specifications, drawings and abstracts are incorporated herein by reference in their entirety.

BACKGROUND OF THE INVENTION

1. Field of the Invention

The invention relates to a surface inspection apparatus for determining whether defects, such as minute protrusions or recesses, are present on a flat, smooth surface, such as a surface of an automobile body coated with a paint film.

2. Description of the Related Art

On production lines of automobile factories, for example, an inspecting operation to check if defects, such as minute protrusions or recesses, are present on a paint film surface of an automobile body is conducted through direct, visual inspection of the paint film surface by a worker.

Also, four methods, namely, 1) inspection using diffusion-type flat lighting, 2) inspection using parallel-beam lighting, 3) inspection using diffusion-type flat lighting with a pattern, and 4) inspection using a plurality of small illuminators arranged in a row, have been implemented as methods for inspecting a surface state or condition.

A surface state evaluation apparatus that quantitatively evaluates the painting or coating quality is disclosed in Japanese Patent Application Publication No. 2003-28805 (JP-A-2003-28805). The surface state evaluation apparatus disclosed in JP-A-2003-28805 includes illuminating means having a plurality of illuminators that are positioned such that light beams emitted from the respective illuminators are incident upon an object to be measured at different incidence angles, control means for switching the illuminators of the illuminating means in time sequence so that the object is irradiated with the illumination light emitted in turn from the illuminators, imaging means for capturing reflected light beams from the object so as to create corresponding images, and evaluation value calculating means for calculating evaluation values representing reflection characteristics of a surface of the object based on changes in the incidence angle of the illumination light.

Also, an inspection apparatus that conducts an inspection on an object for defects, using image data captured by a camera, is disclosed in Japanese Patent Application Publication No. 11-237210 (JP-A-11-237210). The inspection apparatus disclosed in JP-A-11-237210 includes a dispersion optical system that disperses incident light in different directions in correspondence with three different wavelength ranges, an imaging device that images light of each of the wavelength ranges into which the incident light is dispersed, illuminating means having three illuminators to which the three different wavelength ranges into which the incident light is dispersed by the dispersion optical system are assigned, and inspecting means for turning on these illuminators at the same time so as to enable the imaging device to image the light of each wavelength range, and conducting an inspection on the object for detects, based on image data obtained by the imaging device.

The above-mentioned visual inspection conducted by a worker imposes a great physical burden on the worker, and it is thus difficult for the worker to continue the inspecting operation for a long time, which makes it difficult to increase the productivity. Also, the visual inspection depends largely on the ability or efficiency of the worker, and the inspection quality varies to a great extent from one worker to another, which makes it difficult to maintain uniform quality.

In the case of the inspection using the diffusion-type flat lighting as mentioned above at 1), if the area of the surface illuminated is increased, the light diffracts in all directions at minute protrusions or recesses, such as blisters on a painted surface, and the protrusions or recesses do not appear as feature points, resulting in reduced inspection capability. If the area of the surface illuminated is reduced so as to avoid diffraction of light, an area or range inspected by one inspecting operation is considerably narrowed, and the inspection of a coated surface having a large area (for example, about 10 square meters), such as that of an automobile body, cannot be completed within a tact time (for example, about 60 seconds) of a conveyor carrying the object to be inspected.

If the inspection using the parallel-beam lighting as mentioned above at 2) is employed, the directivity of the light can be controlled, and therefore the diffraction of the light, which is a shortcoming of the above type of lighting 1), can be avoided. However, if the object to be inspected has a curved surface, the area over which specularly reflected light is received by a light-receiving portion is reduced, and the field of view covered by one inspecting operation is considerably narrowed. Thus, as in the case 1) above, the inspection of a surface having a large area, such as that of an automobile body, cannot be completed within a tact time of the conveyor. Also, metallic powder or mica contained in a coating may be erroneously detected as defects, depending on the orientation of the metallic powder or mica.

In the case of the inspection using the diffusion-type flat lighting with a pattern as mentioned above at 3), the detection capability is improved as compared with the above type of inspection 1), and the inspection speed is increased as compared with the above type of inspection 2). However, there is a problem in the detection accuracy at boundaries between light and dark portions of the pattern. To solve this problem, two or more cameras are mounted in one unit, so as to shift the phase of the light and dark pattern. However, the same number of image processing boards, personal computers, lenses, and other devices as that of the cameras is required, resulting in increase of the investment cost.

In the case of the inspection using a plurality of small illuminators arranged in a row as mentioned above at 4), the plurality of illuminators need to be turned on one by one so as to enable a camera to take pictures, with respect to one point on the object to be inspected. Accordingly, the movement of the object to be inspected needs to be stopped each time the inspection is conducted on one point, resulting in reduction of the inspection speed. Also, if high-speed photographing is conducted, the quantity of light is reduced, and therefore the SN ratio is reduced.

In the case of the technology described in JP-A-2003-28805, it is necessary to switch the plurality of illuminators in time sequence with respect to one point on the object to be inspected, and cause the imaging means to image the reflected light each time the illuminators are switched from one to another. Thus, it takes much time to capture images, resulting in reduction of the inspection speed.

In the case of the inspection apparatus described in JP-A-11-237210, reflected light from a defect containing surface of an object to be inspected may not be imaged by the imaging means, depending on how each of the illuminators is positioned, resulting in reduced inspection accuracy.

Also, if the relationship in angular position between the object to be inspected and the illuminating means, or the relationship in angular position between the object to be inspected and the imaging device is changed, reflected light that is specularly reflected by the object may not be imaged by the imaging means. Thus, the inspection apparatus is susceptible to inclinations or changes in the angular positions of its components, and the illuminating means and the imaging means are required to be positioned with high accuracy with respect to the object to be inspected.

Accordingly, it is difficult to inspect the entire surface of an object, such as an automobile body, having a considerably large area, while keeping the illuminating means and the imaging device in their correct angular positions, and the inspection apparatus cannot be appropriately used for detection of defects in the form of minute protrusion or recesses.

Referring to FIG. 25 through FIG. 28C, the relationship between the ability to detect a defect Wb and the inspection speed in the related art of the invention will be explained.

In FIG. 25-FIG. 28C showing the manners of detecting a defect Wb, an illuminating means is positioned so as to be opposed to an inspection surface Wa of a body W to be inspected, and the inspection surface Wa is irradiated by the illuminating means, so that reflected light that is reflected by the inspection surface Wa is captured and imaged by imaging means, for detection of a defect Wb.

For example, when a combination of an area camera 201 and an illuminating means 202 having a relatively large illumination size is used, as shown in FIG. 25, a relatively large area or range of the inspection surface Wa can be photographed at a time by the area camera 201, and the range photographed per unit time can be increased.

However, if the illumination size of the illuminating means is relatively large with respect to the defect Wb, as is the case with the illuminating means 202, the area camera 201 receives reflected light C1 as a result of specular reflection of illumination light by portions of the inspection surface Wa other than the defect Wb, and also receives reflected light C2 as a result of specular reflection of illumination light by inclined portions of the defect Wb. Accordingly, the defect Wb may be embedded in the reflected light beams C1, C2, and the defect Wb may not clearly appear in an image captured by the area camera 201.

If, on the other hand, an illuminating means 203 having a relatively small illumination size with respect to the defect Wb is used, as shown in FIG. 26, for example, reflected light C3 as a result of specular reflection of illumination light by inclined portions of the defect Wb is prevented from being captured and imaged by the area camera 201.

Accordingly, the quantity of the reflected light that is reflected by the defect Wb and imaged by the area camera 201 can be made smaller than the quantity of the reflected light that is reflected by other portions of the inspection surface Wa than the defect Wb and imaged by the area camera 201. In the resulting image, the defect Wb appears to be dark as compared with the other portions of the inspection surface Wa than the defect Wb. Thus, a contrast can be produced between the defect Wb and the remaining portions of the inspection surface Wa, and the defect Wb can be indicated clearly.

However, the illuminating means 203 has a narrower illumination range than the illuminating means 202, and the range that can be photographed per unit time is small. Therefore, it takes too much time and impractical to detect defects Wb in the form of minute protrusions or recesses on the inspection surface Wa of the body W, such as an automobile body, having a considerably large area.

In view of the above situation, a line camera 211 may be used in place of the area camera 201, and combined with the illuminating means 203, as shown in FIG. 27A-FIG. 27C, for example. In operation, the line camera 211 and the illuminating means 203 are moved relative to a body W to be inspected, so as to scan an inspection surface Wa of the body W. In this case, the range that can be photographed per unit time can be increased as compared with the case where the area camera 201 is used, because the line camera 211 generally has a greater frame rate than the area camera 201, and is able to capture image data in a shorter time. Accordingly, the defect Wb can be detected in a relatively short time.

However, the line camera 21 captures an image over an extremely small range as measured in the direction of movement of the camera 211. Therefore, if the angles of the line camera 211 and the illuminating means 203 relative to the inspection surface Wa deviate from preset reference angles, as shown in FIG. 28 by way of example, specularly reflected light C4 cannot be captured and imaged by the line camera 211.

Thus, the acceptable degrees of inclination of the line camera 211 and the illuminating means 203 relative to the inspection surface Wa of the body W to be inspected are small. Namely, the inspection apparatus of the related art is susceptible to changes in the angles of the line camera 211 and the illuminating means 203 relative to the inspection surface Wa of the body W, and has a narrow adaptive range with respect to changes in these angles.

SUMMARY OF THE INVENTION

The present invention provides a surface inspection apparatus for quickly and easily detecting defects on a surface of a body to be inspected with high accuracy.

One aspect of the invention is concerned with a surface inspection apparatus, which includes an irradiating unit that has a plurality of light sources that respectively emit a plurality of illumination light beams having different wavelength ranges, and irradiates an inspection surface as a surface of a body to be inspected with the illumination light beams, in a condition where the light sources are located adjacent to each other and arranged in a given order along the inspection surface, an imaging unit that images reflected light when the illumination light beams are reflected by the inspection surface, so as to obtain a plurality of items of image data corresponding to the respective wavelength ranges, and a control unit that detects a detection object on the inspection surface, based on the items of image data corresponding to the respective wavelength ranges which are obtained by the imaging unit.

According to the above arrangement, the irradiating unit is arranged to irradiate the inspection surface with the illumination light beams having different wavelength ranges in a condition where the light sources are located adjacent to each other and arranged in the given order along the inspection surface. Therefore, the angular range over which the reflected light can be imaged by the imaging unit is expanded, and the tolerance of the angle of the irradiating unit or the imaging unit relative to the inspection surface is increased. Accordingly, even if the width of the illumination light beam emitted from each light source as viewed in the direction of arrangement of the light sources is reduced, the reflected light can be imaged, thus assuring an improved ability to detect a detection object.

In the surface inspection apparatus according to the above aspect of the invention, a width of each of the illumination light beams as viewed in a direction in which the light sources are arranged may be determined depending on the size of the detection object. With this arrangement, the width of each illumination light beam as viewed in the direction of arrangement of the light sources is determined depending on the size of the detection object, so that a contrast is produced between the defect and the remaining portion of the inspection surface, and the defect can be clearly indicated or presented.

In the surface inspection apparatus according to the above aspect of the invention, when the detection object comprises a protrusion/recess defect on the inspection surface, the width of each of the illumination light beams may be determined based on a distance from the irradiating unit to the inspection surface and the maximum angle of inclination of the protrusion/recess defect with respect to the inspection surface. In this case, the width of each of the illumination light beams may be equal to or smaller than a product of the distance from the irradiating unit to the inspection surface and a tangent of a doubled value of the maximum inclination angle of the protrusion/recess defect. With this arrangement, reflected light that is specularly reflected by inclined portions of the protrusion/recess defect, as a part of the reflected light originating from the light source opposed to the protrusion/recess defect, is prevented from being imaged by the imaging unit, and a contrast is produced between the defect and the remaining portion of the inspection surface, so that the defect can be clearly indicated or presented.

Also, in the surface inspection apparatus according to the above aspect of the invention, the light sources may be arranged in such an order that a difference in the wavelength range between the illumination light beams emitted from adjacent ones of the light sources is larger than that between the illumination light beams emitted from the other combinations of the light sources. With this arrangement, the imaging unit images reflected light from a certain light source without being greatly affected by light beams emitted from its adjacent light sources even if the imaging unit does not have high dispersion accuracy, and a defect, or the like, can be detected with high accuracy.

In the surface inspection apparatus according to the above aspect of the invention, the irradiating unit may further have an intermediate light source which is placed between two adjacent ones of the light sources and is adapted to emit an illumination light beam having a wavelength range intermediate between the wavelength ranges of the illumination light beams emitted from the two adjacent light sources. In some cases, reflected light that is originally emitted from a boundary portion between two adjacent light sources is captured and imaged by the imaging unit, depending on the relative angle between the inspection surface and the irradiating unit, or the relative angle between the inspection surface and the imaging unit. With the above arrangement, reflected light originally emitted from the intermediate light source and having a stable wavelength range can be imaged by the imaging unit, and otherwise possible reduction in the accuracy of detection of protrusion/recess defects can be avoided.

In the surface inspection apparatus as described above, each of the light sources may consist of a plurality of light emitters having the same wavelength range, and the intermediate light source may have a plurality of light emitters having the same wavelength ranges as those of the two adjacent light sources. Furthermore, the light emitters of the intermediate light source having the same wavelength range as that of one of the two adjacent light sources and the light emitters of the intermediate light source having the same wavelength range as that of the other light source may be arranged in a mixed fashion.

In the surface inspection apparatus according to the above aspect of the invention, the irradiating unit may further have a diffusion plate having a plurality of single-color light emitting regions each of which allows the illumination light beam emitted from each of the light sources to pass therethrough, and at least one intermediate light emitting region that is provided between the plurality of single-color light emitting regions and that emits an illumination light beam of an intermediate color obtained by mixing the light beam emitted from one of two adjacent ones of the light sources with the light beam emitted from the other of the two adjacent light sources.

In the surface inspection apparatus according to the above aspect of the invention, the control unit may identify the detection object, based on a specular reflection amount and a diffuse reflection amount obtained with respect to each wavelength range of the reflected light imaged by the imaging unit. In this connection, it is to be noted that the specular reflection amount for each wavelength range of reflected light varies with the surface state or shape and the specular reflectance, and the diffusion reflection amount varies with the diffusion reflectance that is influenced by a color, or the like, of the inspection surface. Accordingly, the detection object can be easily identified by analyzing the pattern of specular reflection amounts and diffuse reflection amounts for respective wavelength ranges.

In the surface inspection apparatus as described above, the detection object may be identified by using a pattern analysis table that defines the relationship between each of a plurality of types of detection objects, and the specular reflection amount and diffuse reflection amount for each wavelength range of the reflected light. The above-indicated plurality of types of detection objects may include at least one of a protrusion/recess defect, a color defect, a foreign matter, and a design feature.

In the surface inspection apparatus according to the above aspect of the invention, the irradiating unit and the imaging unit may move as a unit in a given direction while keeping a specified distance from the inspection surface.

In the surface inspection apparatus as described just above, the light sources may be arranged in the above-indicated given direction.

In the surface state inspection apparatus according to the above aspect of the invention, the above-indicated plurality of illumination light beams may include red visible light, blue visible light, and green visible light.

According to the present invention, the irradiating unit is arranged to irradiate the inspection surface with the illumination light beams having different wavelength ranges in a condition where the light sources that emit the illumination light beams are located adjacent to each other and arranged in the given order along the inspection surface. Therefore, the angular range over which the reflected light can be imaged by the imaging unit is expanded, and the tolerance of the angle of the irradiating unit or the imaging unit relative to the inspection surface is increased. Accordingly, even if the width of the illumination light beam emitted from each light source as measured in the direction of arrangement of the light sources is reduced, the reflected light can be imaged, and the ability to detect a detection object can be improved.

BRIEF DESCRIPTION OF THE DRAWINGS

The foregoing and further objects, features and advantages of the invention will become apparent from the following description of example embodiments with reference to the accompanying drawings, wherein like numerals are used to represent like elements and wherein:

FIG. 7A through FIG. 7D are schematic views of images captured by the imaging unit when the apparatus is in the operating condition as shown in FIG. 6;

FIG. 11 is a view illustrating a specific example of the second embodiment;

FIG. 12 is a view explaining another specific example of the second embodiment;

FIG. 13 is a flowchart illustrating a method of detecting an object and identifying the detected object;

FIG. 14 is a view showing a pattern analysis table;

FIG. 16A-FIG. 16C are schematic views showing image data for each of the wavelength ranges into which the color image of FIG. 15B is dispersed;

FIG. 16D-FIG. 16F are views showing brightness distribution data of each image of FIG. 16A-FIG. 16C, respectively;

FIG. 18A-FIG. 18C are schematic views showing image data for each of the wavelength ranges into which the color image of FIG. 17B is dispersed;

FIG. 18D-FIG. 18F are views showing brightness distribution data of each image of FIG. 18A-FIG. 18C, respectively;

FIG. 20A-FIG. 20C are schematic views showing image data for each of the wavelength ranges into which the color image of FIG. 19B is dispersed;

FIG. 20D-FIG. 20F are views showing brightness distribution data of each image of FIG. 20A-FIG. 20C, respectively;

FIG. 22A-FIG. 22C are schematic views showing image data for each of the wavelength ranges into which the color image of FIG. 21B is dispersed;

FIG. 22D-FIG. 22F are views showing brightness distribution data of each image of FIG. 22A-FIG. 22C, respectively;

FIG. 24A-FIG. 24C are schematic views showing image data for each of the wavelength ranges into which the color image of FIG. 23B is dispersed;

FIG. 24D-FIG. 24F are views showing brightness distribution data of each image of FIG. 24A-FIG. 24C, respectively;

DETAILED DESCRIPTION OF EMBODIMENTS

A first embodiment of the invention will be described with reference to the drawings.

Figure 1:
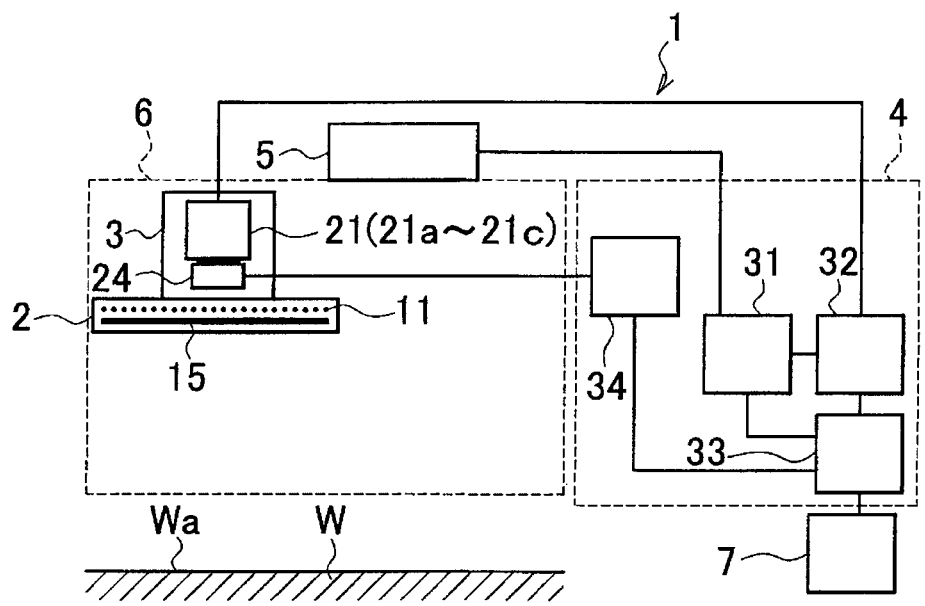
FIG. 1 is a block diagram illustrating the overall construction of a surface inspection apparatus according to a first embodiment of the invention.
Figure 2:
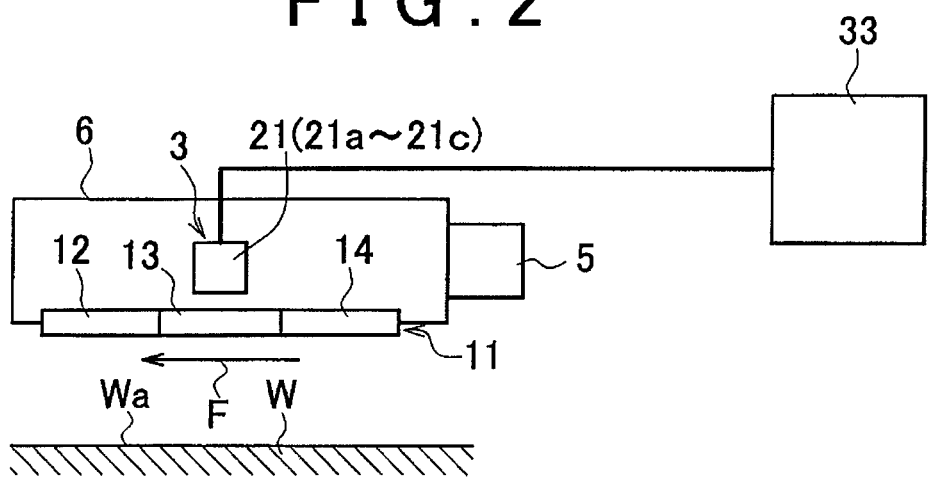
FIG. 2 is a conceptual view useful for explaining the construction of a sensor unit.
Figure 3:
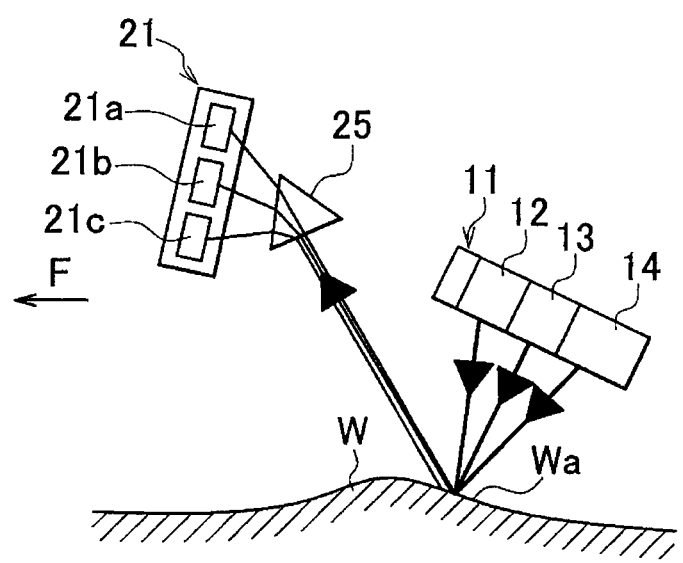
FIG. 3 is a view schematically illustrating a method of inspecting a surface state by means of the surface inspection apparatus.

FIG. 1 is a block diagram illustrating the overall construction of a surface inspection apparatus 1 according to the first embodiment of the invention, and FIG. 2 is a conceptual view useful for explaining the construction of a sensor unit 6, while FIG. 3 is a view schematically showing a method of inspecting a surface state or profile by means of the surface inspection apparatus 1. The surface inspection apparatus 1 of this embodiment is characterized in that the acceptable ranges of inclinations of a line camera 21 and an illuminating device 11 with respect to an inspection surface Wa of a body W to be inspected are large.

As shown in FIG. 1, the surface inspection apparatus 1 has an irradiating unit 2 that emits a plurality of illumination light beams R, B having mutually different wavelength ranges, an imaging unit 3 that captures images of an inspection surface Wa of a body W to be inspected which is illuminated by the illumination light beams R, G, B from the irradiating unit 2, a control unit 4 that detects a defect Wb on the inspection surface Wa based on image data representing the images captured by the imaging unit 3, and a result display unit 7 that displays the result of detection obtained by the control unit 4.

The irradiating unit 2 and the imaging unit 3 are provided in a sensor unit 6 attached to a distal end of a robot arm 5, such that these units 2, 3 are fixed integrally to the sensor unit 6. With the robot arm 5 controlled, the sensor unit 6 is moved in a preset sensor movement direction F along the inspection surface Wa, while keeping a constant distance or spacing from the inspection surface Wa of the body W to be inspected, as shown in FIG. 2.

The irradiating unit 2 includes an illuminating means 11 and a diffusion plate 15, as shown in FIG. 1. In this embodiment, the illuminating means 11 has three light sources 12, 13, 14 arranged in this order in the sensor movement direction F, as shown in FIG. 2.

The light sources 12, 13, 14 are adapted to emit illumination light beams having different wavelength ranges. In this embodiment, the light source 12 emits red light, and the light source 13 emits blue light, while the light source 14 emits green light. Thus, the illuminating means 11 is adapted to emit illumination light beams of RGB (R: red, G: green, B: blue) as the primary colors of light.

The light sources 12, 13, 14 are positioned such that the wavelength ranges of the light beams emitted from adjacent ones of the light sources are different largely from each other.

Figure 4A:
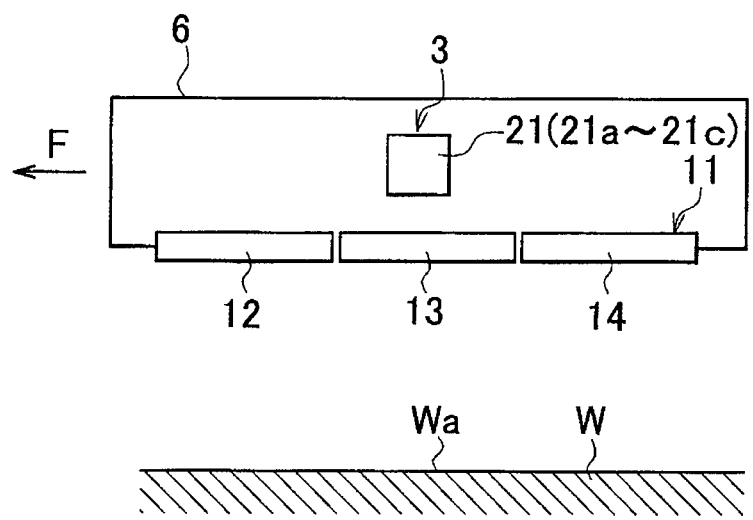
FIGS. 4A and 4B are views useful for explaining the order in which light sources are arranged.
Figure 4B:
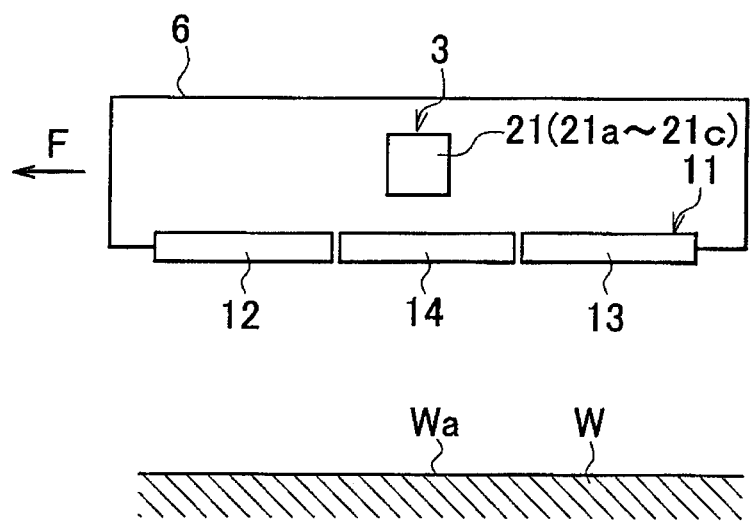

FIG. 4A and FIG. 4B are views explaining the order in which the light sources 12, 13, 14 are arranged. FIG. 4A shows the arrangement of this embodiment, and FIG. 4B shows the arrangement of a comparative example.

With regard to the illumination light beams emitted from the respective light sources 12, 13, 14, the red light R has a frequency of about 640 nm, and the blue light B has a wavelength of about 470 nm, while the green light G has a wavelength of about 530 nm. In the case where the light sources 12, 13, 14 are positioned such that the wavelength ranges of light beams emitted from adjacent light sources are close to each other (i.e., where the red light source 12, green light source 14, and blue light source 13 are arranged in this order from the front to the rear in the sensor movement direction F), as shown in the comparative example of FIG. 4B, the detection performance or accuracy may deteriorate due to an influence of a light beam of an adjacent light source when the light reflected by the inspection surface is dispersed into a spectrum.

In this embodiment, on the other hand, the red light source 12, blue light source 13 and green light source 14 are arranged in this order from the front to the rear in the sensor movement direction F, as shown in FIG. 4A. Accordingly, even if the imaging unit 3 does not have a high spectral sensitivity or accuracy, it is less likely to be influenced by a light beam of an adjacent light source, thus assuring high detection accuracy.

Although not particularly illustrated in the drawings, each of the light sources 12, 13, 14 is arranged to extend in a straight line over a given length, in a lateral direction perpendicular to the sensor movement direction F. In this embodiment, a line illuminator using LEDs (Light Emitting Diodes) of each color is used.

The diffusion plate 15, which is placed between the illuminating means 11 and the body W to be inspected as shown in FIG. 1, allows the illumination light emitted from the light sources 12, 13, 14 of the illuminating means 11 to pass therethrough, thereby to control the directivity of the light.

The imaging unit 3 includes a line camera 21, a lens system 24, and a prism 25 (see FIG. 3), as shown in FIG. 1. The line camera 21 is in the form of a linear array sensor for capturing color images, and has three CCDs (Charge Coupled Device) 21a, 21b, 21c for detecting red light, blue light and green light, respectively, as shown in FIG. 3.

Each of the CCDs 21a, 21b, 21c of the line camera 21 extends in a straight line over a given length, in a lateral direction perpendicular to the sensor movement direction F, and the CCDs 21a, 21b, 2c are arranged in parallel with the light sources 12, 13, 14. The angles and positions of the CCDs 21a, 21b, 21c are set so that the CCDs 21a, 21b, 21c respectively receive light beams emitted from the respective light sources 12, 13, 14 and specularly reflected by the inspection surface Wa when the sensor unit 6 is positioned in a predetermined orientation with respect to the inspection surface Wa of the body W to be inspected, to be opposed to the inspection surface Wa. The CCDs 21a, 21b, 21c thus positioned capture images of the inspection surface Wa irradiated with the light sources 12, 13, 14, so as to acquire image data.

The lens system 24 is arranged to adjust the focus of the line camera 21 on the inspection surface Wa, as shown in FIG. 1. The prism 25 functions to disperse reflected light that is specularly reflected by the inspection surface Wa in different directions corresponding to three different wavelength ranges, as shown in FIG. 3, so that red light R as a component of the reflected light is received by the CCD 21a for detecting red light, and blue right B as another component of the reflected light is received by the CCD 21b for detecting blue light, while green light G as a further component of the reflected light is received by the CCD 21c for detecting green light.

The control unit 4 consists of a computer or an electronic circuit device, or the like, which is housed in a control board (not shown). The control unit 4 executes control programs, so as to serve as a light source control means 31, camera control means 32, image processing means 33 and a lens aperture control means 34, as its internal functions.

The light source control means 31 controls lighting of each light source 12, 13, 14 of the illuminating means 11, and the camera control means 32 controls imaging or image capturing of the line camera 21. The image processing means 33 processes image data captured by the line camera 21, so as to extract or detect defects Wb in the form of protrusions and recesses on/in the inspection surface, and the lens aperture control means 34 adjusts an aperture (f-number) of the lens system 24.

Figure 5:
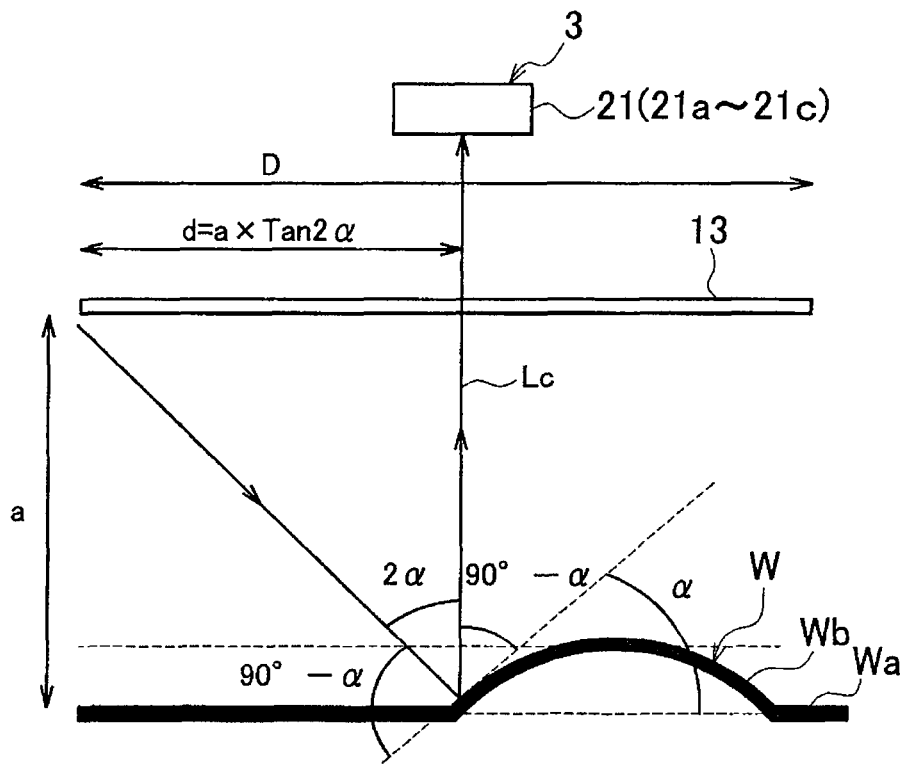
FIG. 5 is a view illustrating a method of setting a width of a light source.

FIG. 5 is a view explaining a method of setting the width of each light source of the illuminating means. The width "D" of each light source 12, 13, 14 as viewed in the sensor movement direction (the width as viewed in the direction of arrangement of the light sources) is determined by a distance between the light source 12, 13, 14 and the inspection surface Wa. For example, if the distance between the blue light source 13 and the inspection surface Wa is equal to "a", as shown in FIG. 5, distance "d" (=D/2) as a half of the width D as viewed in the sensor movement direction, i.e., distance "d" from the center axis Lc of the blue light source 13 to one end of the light source, is geometrically determined according to the following equation (1).

$$d = a \times \tan 2\alpha \tag{1}$$

Then, the width D of the blue light source 13 as viewed in the sensor movement direction is obtained by doubling the distance d (D=2a× tan 2α). The width of the red light source 12 and that of the green light source 14 may be determined in the same manner.

In the above-indicated equation (1), "α" is the maximum angle of inclination of a surface of a defect Wb with respect to the inspection surface Wa. For example, where a defect Wb shaped like a protrusion (having a width of about 0.2 mm and a height of about 3 μm, for example) is formed on the inspection surface Wa, a rising portion of the defect Wb is inclined at the maximum angle of inclination "α".

Thus, the width "D" of each light source 12, 13, 14 is determined by the distance "a" between the light source 12, 13, 14 and the inspection surface Wa. Accordingly, if the distance "a" is set to a small value, for example, the width "D" can be reduced, which leads to reduction in the size of each of the light sources 12, 13, 14 and reduction in the cost of the illumination equipment.

Next, an inspection method using the surface inspection apparatus 1 constructed as described above will be described. Initially, when the control unit 4 receives color information (light reflecting characteristics) of the inspection surface Wa of the body W to be inspected, the light source control means 31 adjusts a lighting duration of each light source 12, 13, 14 of the illuminating means 11, and a value of current passed through each light source, and the light sources 12, 13, 14 are turned on at the same time. Then, the camera control means 32 controls an exposure time and gain of the line camera 21, and the lens aperture control means 34 adjusts the aperture (f-number) of the lens system 24.

Then, the robot arm 5 moves the sensor unit 6 while keeping a certain distance between the sensor unit 6 and the body W to be inspected. When the sensor unit 6 reaches a specified point, an imaging start signal is sent to the camera control means 32, so that the imaging unit 3 starts capturing images.

The sensor unit 6 is moved by the robot arm 5 in the sensor movement direction F while keeping a constant camera distance from the inspection surface Wa. The imaging unit 3 captures an image of the inspection surface Wa irradiated with the light beams from the red light source 12, blue light source 13 and the green light source 14.

The reflected light carrying the image of the inspection surface Wa irradiated with the light beams from the red light source 12, blue light source 13 and the green light source 14 is dispersed by the prism 25 into light beams of respective wavelength ranges of RGB, and images formed by the light beams of the respective wavelength ranges of RGB are captured by the respective CCDs 21a, 21b, 21c of the line camera 21.

The image processing unit 33 performs image processing on the images captured by the respective CCDs 21a, 21b, 21c, so that a portion of the image where the reflected light is not incident upon the imaging unit 3 is displayed in a dark color, and the dark portion is extracted as a defect Wb. Then, the position and image, or the like, of the defect Wb are displayed on the result display unit 7.

Figure 6:
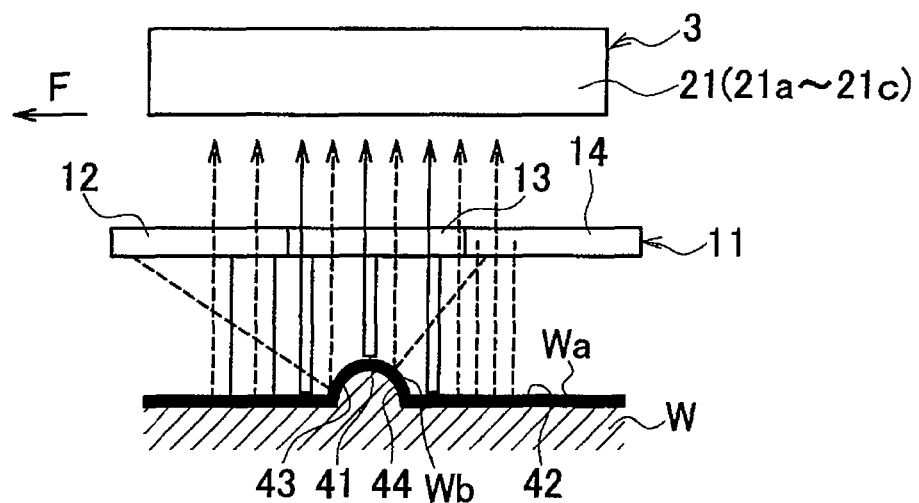
FIG. 6 is a view showing an operating condition of the apparatus for presenting a protrusion/recess defect as a contrast to the remaining portion of an inspection surface.

FIG. 6 is a view showing how a defect Wb is presented as a contrast in images captured, and FIG. 7A through FIG. 7D are schematic views of images captured by the imaging unit 3 in a condition shown in FIG. 6.

FIG. 7A schematically shows a color image obtained before the reflected light is dispersed by the prism 25, and FIG. 7B schematically shows an image captured by the CCD 21a for detecting red light, while FIG. 7C schematically shows an image captured by the CCD 21b for detecting blue light, and FIG. 7D schematically shows an image captured by the CCD 21c for detecting green light.

In a condition as shown in FIG. 6 where the blue light source 13 of the illuminating means 11 is opposed to a defect Wb of the body W to be inspected, for example, blue light B specularly reflected by an inclined portion 43 as a front portion of the defect Wb as viewed in the sensor movement direction F and blue light B specularly reflected by an inclined portion 44 as a rear portion of the defect Wb as viewed in the sensor movement direction F are not incident upon the imaging unit 3, namely, are not received by the imaging unit 3.

On the other hand, the imaging unit 3 receives red light R of the red light source 12 which is specularly reflected by the inclined portion 43 as the front portion of the defect Wb as viewed in the sensor movement direction F, and receives green light G of the green light source 14 which is specularly reflected by the inclined portion 44 as the rear portion of the defect Wb as viewed in the sensor movement direction F.

In the color image, therefore, a top portion 41 of the defect Wb and a flat or smooth portion 42 other than the defect Wb are indicated in blue color B, and the inclined portion 43 of the defect Wb is indicated in red color R, while the inclined portion 44 of the defect Wb is indicated in green color as shown in FIG. 7A.

In a monochrome image captured by the CCD 21a for detecting red color, the inclined portion 43 of the defect Wb is displayed in light color, and the remaining portion other than the inclined portion 43 is displayed in dark color, as shown in FIG. 7B. In a monochrome image captured by the CCD 21b for detecting blue color, the inclined portions 43, 44 of the defect Wb are displayed in dark color, and the remaining portion other than the inclined portions 43, 44 is displayed in light color, as shown in FIG. 7C. In a monochrome image captured by the CCD 21c for detecting green color, the inclined portion 44 of the defect Wb is displayed in light color, and the remaining portion other than the inclined portion 44 is displayed in dark color, as shown in FIG. 7D. Accordingly, the defect Wb can be contrasted with the other portion, and the image processing means 33 can easily extract the defect Wb.

Figure 8A:
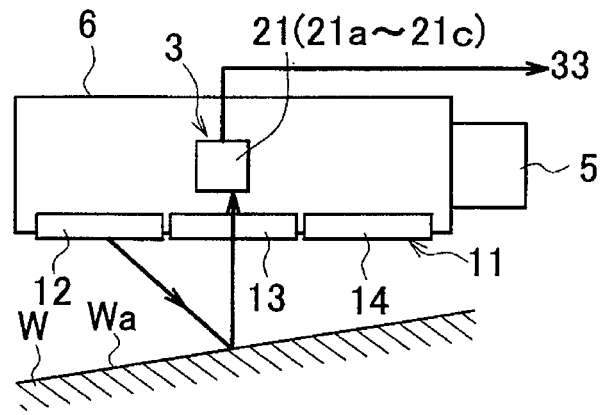
FIG. 8A through FIG. 8C are views useful for explaining the operation and effect provided according to the first embodiment of the invention.
Figure 8B:
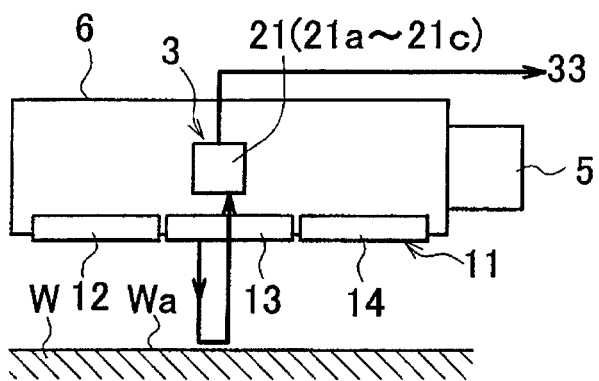
Figure 8C:
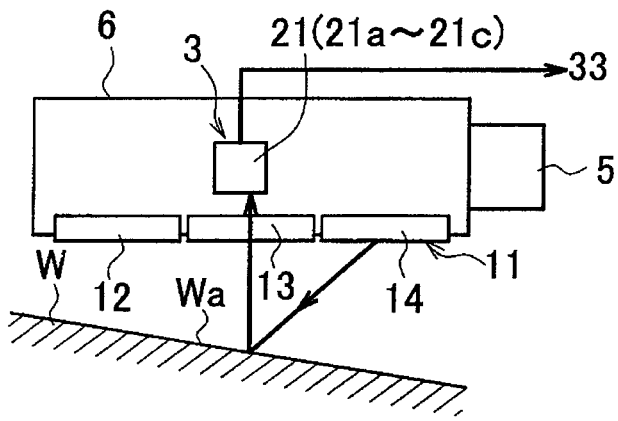
Figure 9A:
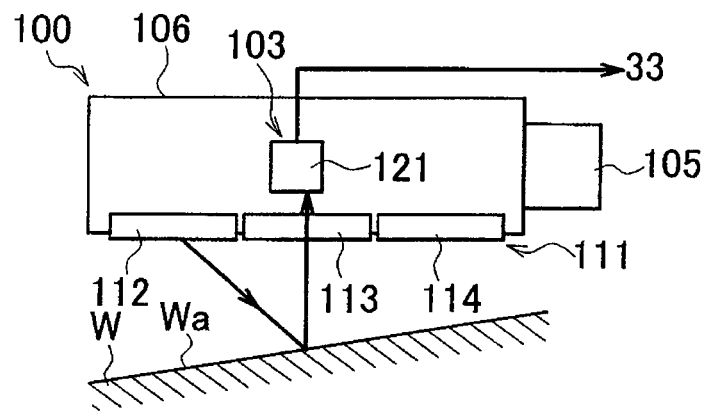
FIG. 9A through FIG. 9C are views showing a comparative example for comparison with FIG. 8A through FIG. 8C.
Figure 9B:
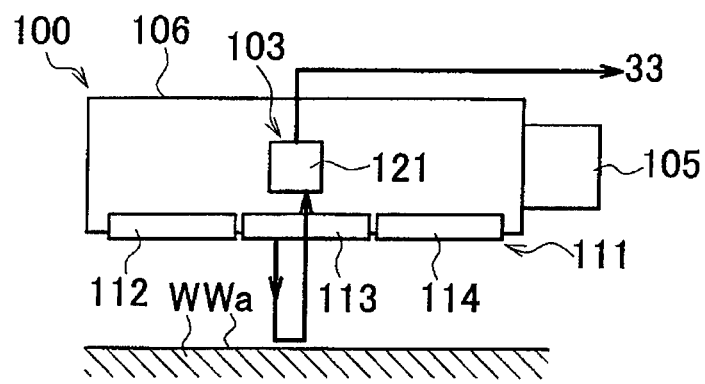
Figure 9C:
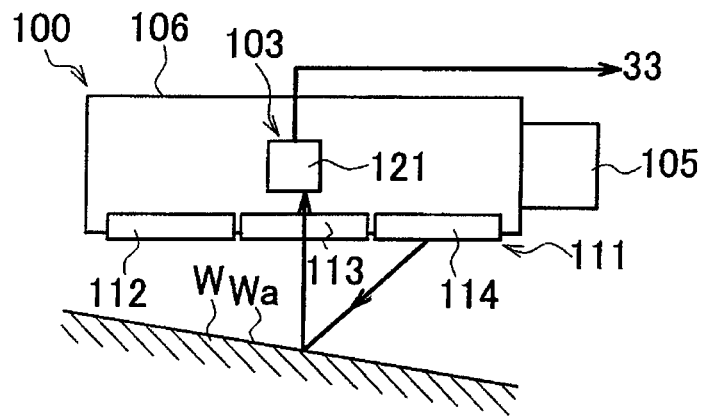

Next, the operation and effect of the surface inspection apparatus 1 of this embodiment will be described. FIG. 8A-FIG. 8C are views useful for explaining the operation and effect of this embodiment, while FIG. 9A-FIG. 9C are views showing a comparative example for comparison with FIG. 8A-FIG. 8C.

In the surface inspection apparatus 1 of this embodiment, when the sensor unit 6 is positioned in a preset orientation to be opposed to the inspection surface Wa of the body W to be inspected, as shown in FIG. 8B, blue light B emitted from the blue light source 13 is specularly reflected by the inspection surface Wa, and the reflected light is received by the CCD 21b for detecting blue light. If a defect Wb is present on the inspection surface Wa, inclined portions of the defect Wb are displayed in dark color in a monochrome image captured by the CCD 21b for detecting blue light. Accordingly, the defect Wb can be clearly recognized.

If the sensor unit 6 is inclined from the preset orientation in which the sensor unit 6 is opposed to the inspection surface Wa, and the spacing between the sensor unit 6 and the inspection surface Wa decreases from the front to the rear in the sensor movement direction F, as shown in FIG. 8A, red light R emitted from the red light source 12 is specularly reflected by the inspection surface Wa, and the reflected light can be received by the CCD 21a for detecting red light. If a defect Wb is present on the inspection surface Wa, an inclined portion of the defect Wb is displayed in dark color in a monochrome image captured by the red-color CCD 21a. Accordingly, even if the sensor unit 6 is inclined with respect to the inspection surface Wa, as shown in FIG. 8A, a contrast representing the defect Wb can be produced, and the defect Wb can be clearly presented.

If the sensor unit 6 is inclined from the preset orientation in which the sensor unit 6 is opposed to the inspection surface Wa, and the spacing between the sensor unit 6 and the inspection surface Wa decreases from the rear to the front in the sensor movement direction F, as shown in FIG. 8C, green light G emitted from the green light source 14 is specularly reflected by the inspection surface Wa, and the reflected light can be received by the CCD 21c for detecting green light. If a defect Wb is present on the inspection surface Wa, an inclined portion of the defect Wb is displayed in dark color in a monochrome image captured by the green-light CCD 21c. Accordingly, even if the sensor unit 6 is inclined with respect to the inspection surface Wa, as shown in FIG. 8C, a contrast representing the defect Wb can be produced, and the defect Wb can be clearly presented.

In a surface inspection apparatus 100 of the comparative example shown in FIGS. 9A-FIG. 9C, a sensor unit 106 includes an imaging unit 103 and an illuminating means 111 which has three illuminators 112, 113, 114 adapted to emit light beams having the same wavelength range, in place of the light sources 12, 13, 14 used in this embodiment, and is arranged to capture images with a line camera 121 consisting of a single CCD, while switching the illuminators 112, 113, 114 in time sequence. Further, the surface inspection apparatus 100 according to the example shown in FIGS. 9A-FIG. 9C may also include a robot arm 105.

In the comparative example, when the sensor unit 6 is inclined with respect to the inspection surface Wa, as shown in FIG. 9A or FIG. 9C, the reflected light originating from the illuminator 112 or the illuminator 114 can be received by the line camera 121.

However, the illuminators 112, 113, 114 are switched (i.e., used in turn) in time sequence for irradiating one point on the inspection surface Wa, and an image needs to be captured each time switching takes place. Accordingly, it takes much time to capture images, resulting in a reduced inspection speed.

According to the surface inspection apparatus 1 of this embodiment, on the other hand, the light sources 12, 13, 14 are turned on at the same time for capturing of images, so that the time it takes to capture images can be reduced, and the inspection speed can be increased.

In the surface inspection apparatus 1 as described above, the light sources 12, 13, 14 adapted to emit light beams having different wavelength ranges are arranged in the sensor movement direction such that each light source has a suitable width as measured in a direction perpendicular to the sensor movement direction. Also, in the surface inspection apparatus 1, the reflected light that is reflected by the inspection surface Wa is dispersed and received by the line camera 21.

With the above arrangement, it is possible to expand or increase the angular range over which the reflected light can be captured by the imaging unit to form images, and to increase the tolerance of the angle of the irradiating unit 2 or imaging unit 3 relative to the inspection surface Wa. Accordingly, the surface inspection apparatus 1 is less likely to be affected by changes in the relative angle between the inspection surface Wa and the sensor unit 6, and the acceptable degree of inclination of the sensor unit 6 relative to the inspection surface Wa can be increased.

Thus, even where the angle of the sensor unit 6 relative to the inspection surface Wa, namely, the angle of the irradiating unit 2 or imaging unit 3 relative to the inspection surface Wa, is changed due to, for example, fluctuations in the motion of the robot arm 5, at least one of the reflected light beams originating from the plurality of light sources can be received by the imaging unit 3, and a defect(s) Wb can be quickly and correctly detected.

In the surface inspection apparatus 1 of this embodiment in which the reflected light reflected by the inspection surface Wa is dispersed and received by the imaging unit 3, the light sources 12, 13, 14 can be turned on at the same time, and corresponding images can be captured by the line camera 21 at the same time. Therefore, the imaging or picture-taking time of the imaging unit 3 can be shortened, and the inspection speed can be increased.

It is to be understood that the invention is not limited to the first embodiment as described above, but may be embodied with various changes without departing from the principle of the invention. In the illustrated embodiment, the red light source 12, blue light source 13, and the green light source 14 are employed as an example of a plurality of illuminators having different wavelength ranges. However, the illuminators are not limited to these light sources 12, 13, 14 provided that they are able to emit light beams having different wavelength ranges.

While the light sources 12, 13, 14 are arranged in this order from the front to the rear in the sensor movement direction F in the illustrated embodiment, the order in which the light sources are arranged may be changed provided that adjacent ones of the light sources emit light beams having largely different wavelength ranges. For example, the light sources 14, 13, 12 are arranged in this order from the front to the rear in the sensor movement direction F.

Figure 10A:
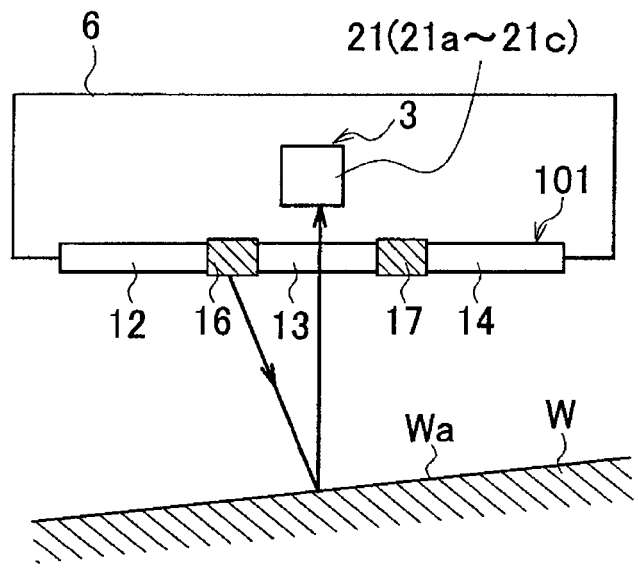
FIG. 10A and FIG. 10B are conceptual views useful for explaining the second embodiment of the invention.
Figure 10B:
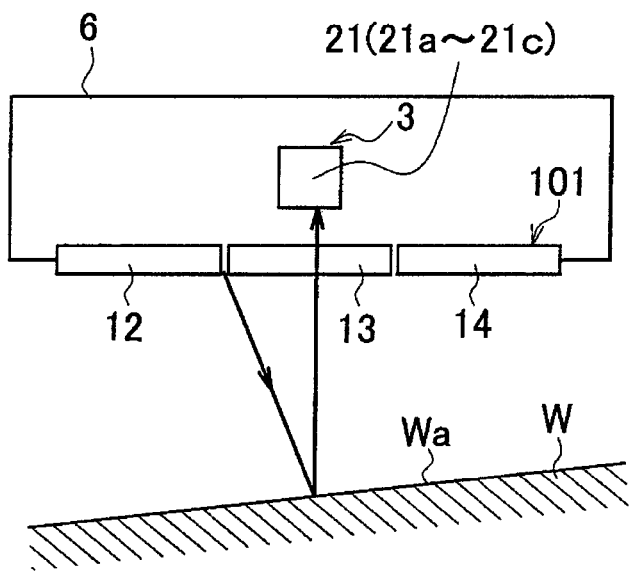

Next, a second embodiment of the invention will be described with reference to FIG. 10A through FIG. 12. FIG. 10A and FIG. 10B are conceptual views useful for explaining the second embodiment. In these figures, the same reference numerals as used in the first embodiment are used for identifying the same or corresponding constituent elements, of which no detailed description will be provided.

A surface inspection apparatus of the second embodiment includes an illuminating device 101 as a modified example of the illuminating means 11 of the first embodiment. For example, if the relative angle between the inspection surface Wa and the sensor unit 6 is changed in the first embodiment, namely, the sensor unit 6 is inclined from a preset orientation in which the sensor unit 6 is opposed to the inspection surface Wa, and reflected light originating from a boundary between the red light source 12 and the blue light source 13 is received by the imaging unit 3, as shown in FIG. 10B, the wavelength range of the reflected light is unstable, and the accuracy with which defects are detected may be reduced.

In the second embodiment, on the other hand, an intermediate light source 16 having both of the wavelength ranges of the light sources 12, 13 is provided between the adjacent light sources 12, 13, and an intermediate light source 17 having both of the wavelength ranges of the light sources 13, 14 is provided between the adjacent light sources 13, 14, as shown in FIG. 10A.

With this arrangement, even when the sensor unit 6 is brought into the above-described inclined position relative to the inspection surface Wa, reflected light having a stable wavelength range can be received by the imaging unit 3, and the accuracy in detection of defects Wb will not be reduced.

FIG. 11 and FIG. 12 show specific examples that implement the second embodiment. The example shown in FIG. 11 utilizes the arrangement of LED emitters 12a, 13a, 14a used as illuminators of the illuminating means 101. The red light source 12 is formed by placing a plurality of red LEDs 12a in a line, and the blue light source 13 is formed by placing a plurality of blue LEDs 13a in a line, while the green light source 14 is formed by placing a plurality of green LEDs 14a in a line.

The intermediate light source 16 is formed between the red light source 12 and the blue light source 13 by alternately placing the red LEDs 12a and the blue LEDs 13a in a line, and the intermediate light source 17 is formed between the blue light source 13a and the green light source 14a by alternately placing the blue LEDs 13a and the green LEDs 14a in a line.

With the above arrangement, illumination light having both of the wavelength ranges of red light R and blue light B can be emitted from the intermediate light source 16, and illumination light having both of the wavelength ranges of blue light B and green light G can be emitted from the intermediate light source 17.

Accordingly, even in a situation where the relative angle between the sensor unit 6 and the inspection surface Wa is changed such that the sensor unit 6 is inclined from the preset orientation in which the sensor unit 6 is opposed to the inspection surface Wa, and reflected light from the boundary between the red light source 12 and the blue light source 13 or between the blue light source 13 and the green light source 14 is received by the imaging unit 3, reflected light having a stable wavelength range, which originates from the intermediate light source 16 or intermediate light source 17, can be received by the imaging unit 3, and otherwise possible reduction in the accuracy of detection of defects Wb can be avoided.

The example shown in FIG. 12 utilizes a diffusion plate 15 as well as the LED emitters 12a, 13a, 14a. In the illuminating means 101 of the irradiating unit 2, the red light source 12 is formed by placing a plurality of red LEDs 12*a* in a line, and the blue light source 13 is formed by placing a plurality of blue LEDs 13*a* in a line, while the green light source 14 is formed by placing a plurality of green LEDs 14*a* in a line. The irradiating unit 2 further includes the diffusion plate 15 that is irradiated with illumination light such that light beams emitted from adjacent illuminators overlap with each other in certain regions.

The diffusion plate 15 allows illumination light beams of the respective light sources 12, 13, 14 to pass therethrough, and emits light beams while controlling the directivity of each light beam during the passage therethrough.

More specifically, the diffusion plate 15 has a red light-emitting region 15R that allows illumination light emitted from the red light source 12 to pass therethrough, thereby to emit only red light R, a blue light-emitting region 15B that allows illumination light emitted from the blue light source 13 to pass therethrough, thereby to emit only blue light B, and a green light-emitting region 15G that allows illumination light emitted from the green light source 14 to pass therethrough, thereby to emit only green light G.

In addition, an intermediate light-emitting region 15RB that emits both red light R and blue light B is formed between the red light-emitting region 15R and the blue light-emitting region 15B, and an intermediate light-emitting region 15BG that emits a mixture of blue light B and green light G is formed between the adjacent blue light-emitting region 15B and green light-emitting region 15G.

With the above arrangement, illumination light having both of the wavelength ranges of red light R and blue light B is emitted from the intermediate light-emitting region 15RB, and illumination light having both of the wavelength ranges of blue light B and green light G is emitted from the intermediate light-emitting region 15BG.

Accordingly, even when the sensor unit 6 is brought into the above-described inclined position relative to the inspection surface Wa, reflected light having a stable wavelength range, which originates from the intermediate light-emitting region 15RB, 15BQ can be received by the imaging unit 3, and otherwise possible reduction in the accuracy of detection of defects Wb can be avoided.

While three types of light sources, i.e., the red light source 12, blue light source 13 and the green light source 14, are used as the plurality of illuminators having different wavelength ranges in each of the illustrated embodiments, a different number or different types of light sources, for example, illuminators having five wavelength ranges, may be used.

Next, a third embodiment of the invention will be described with reference to FIG. 13 through FIG. 24. In these figures, the same reference numerals as used in the above-described embodiments are used for identifying the same or corresponding constituent elements, of which no detailed description will be provided.

In this embodiment, an object detected by the image processing means 33 is identified. More specifically, it is determined whether the object detected by the image processing means 33 is a protrusion/recess defect Wb, a color defect Wc1, Wc2, a foreign matter Wd, such as dust deposited on the inspection surface Wa, or a design feature, such as a hole We formed through the inspection surface Wa, step, or an edge.

The color defect means a point, or the like, which is formed on the inspection surface Wa having a single color or substantially the same color and has a color different from that of the inspection surface Wa. The color defect may be a dark-color defect Wc1 that is a dot-like dark-color portion formed on a light-color panel, or a light-color defect Wc2 that is a light-color dot-like portion formed on a dark-color panel.

The image processing means 33 of the control unit 4 performs processing for identifying the detected object, based on the amount of specular reflection and the amount of diffuse reflection for each wavelength range of reflected light captured and imaged by the line camera 21. The amount of specular reflection of the reflected light varies with a condition of the surface state of the inspection surface Wa, and the amount of diffuse reflection of the reflected light varies with the color of the inspection surface Wa. The image processing means 33 analyzes a pattern of specular reflection amounts and diffuse reflection amounts, based on the brightness distribution for each wavelength range, and selects a pattern matching the result of analysis, from pre-set patterns in a pattern analysis table (i.e., table for use in pattern analysis), so as to identify the detected object.

FIG. 13 is a flowchart explaining a method of detecting an object and identifying the detected object, and FIG. 14 is a view illustrating an example of pattern analysis table. In the pattern analysis table of FIG. 14, the amount of specular reflection and amount of diffuse reflection in each of images corresponding to wavelength ranges of red, blue and green lights are indicated with respect to each type of detected object.

Initially, the inspection surface Wa is irradiated with light emitted from the illuminating means 11 of the irradiating unit 2 (step S101). Then, the line camera 21 receives light reflected by the inspection surface Wa (step S102), so as to obtain a color image of the inspection surface Wa (step S103). Then, the color image is dispersed into a red image, a blue image and a green image as image data for each of the wavelength ranges (step S104).

With regard to each of the obtained images (i.e., image of each wavelength range), the brightness distribution data for each wavelength range of the reflected light is obtained (step S105). A pattern analysis is conducted on the brightness distribution data for each wavelength range (step S106), taking note of the fact that the specular reflectance and the diffusion reflectance vary from one pattern (type) of detected object to another. Then, the detected object is identified, based on the result of the pattern analysis (step S107).

In the pattern analysis of step S106, the pattern analysis table as shown in FIG. 14, for example, is searched for a matching pattern. The pattern analysis table is stored in advance in the control unit 4. If a matching pattern is found, it is determined that the object of the type to which the matching pattern is assigned is detected. If no matching pattern is found, it is determined that the detected object cannot be identified. The control unit 4 displays the result of the determination on the result display unit 7.

Figure 15A:
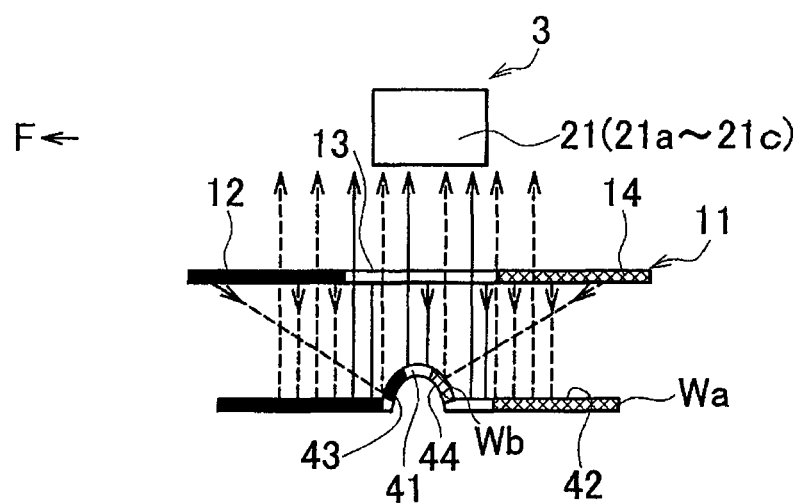
FIG. 15A is a view useful for explaining a method of detecting a protrusion/recess defect.
Figure 15B:
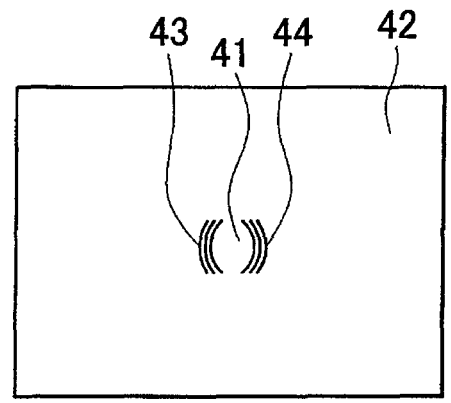
FIG. 15B is a schematic view showing a color image taken in a condition as shown in FIG. 15A.

In a color image taken by the imaging unit 3 when it images a protrusion/recess defect Wb on the inspection surface Wa, as shown in FIG. 15A, a top portion 41 of the defect Wb and a flat portion 42 other than the defect Wb are indicated in blue color B, and an inclined portion 43 of the defect Wb is indicated in red color R, while an inclined portion 44 of the defect Wb is indicated in green color Q as shown in FIG. 15B.

In a monochrome image taken by the CCD 21*a* for red color, the inclined portion 43 of the defect Wb is indicated in light color, and the remaining portion of the image other than the inclined portion 43 is indicated in dark color, as shown in FIG. 16A. Accordingly, the brightness distribution in a section taken along line X-X of FIG. 16A is such that the brightness is outstandingly high only at a position corresponding to the inclined portion 43, as compared with the other portion, as shown in FIG. 16D. In the red-color wavelength range, therefore, the specular reflection amount is large, and the diffuse reflection amount is extremely small.

In a monochrome image taken by the CCD 21b for blue color, the inclined portions 43, 44 of the defect Wb are indicated in dark color, and the remaining portion of the image other than the inclined portions 43, 44 is indicated in light color, as shown in FIG. 16B. Accordingly, the brightness distribution in a section taken along line X-X of FIG. 16B is such that the brightness falls down to a low level at positions corresponding to the inclined portions 43, 44, as compared with the other portion, as shown in FIG. 16E. In the blue-color wavelength range, therefore, the specular reflection amount is small, and the diffuse reflection amount is extremely small.

In a monochrome image taken by the CCD 21c for green color, the inclined portion 44 of the defect Wb is indicated in light color, and the remaining portion of the image other than the inclined portion 44 is indicated in dark color, as shown in FIG. 16C. Accordingly, the brightness distribution in a section taken along line X-X of FIG. 16C is such that the brightness is outstandingly high only at a position corresponding to the inclined portion 44, as compared with the other portion, as shown in FIG. 16F. In the green-color wavelength range, therefore, the specular reflection amount is large, and the diffuse reflection amount is extremely small.

By using the specular reflection amount and diffuse reflection amount for each of the wavelength ranges of red, blue and green colors and referring to the pattern analysis table as shown in FIG. 14, the detected object can be identified as the protrusion/recess defect Wb.

Figure 17A:
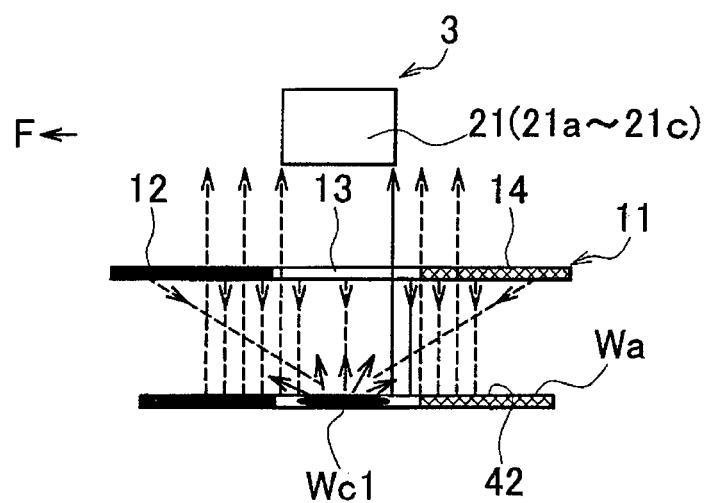
FIG. 17A is a view useful for explaining a method of detecting a color defect (a dark-color defect on light color)
Figure 17B:
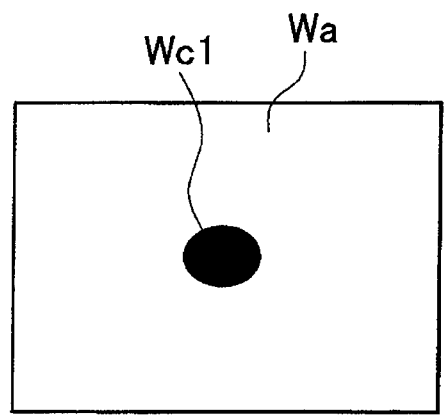
FIG. 17B is a schematic view showing a color image taken by the imaging unit.

When the imaging unit 3 images an inspection surface Wa that is coated with a light-color (e.g., white) paint, where a dot-like dark-color (e.g., black) paint is deposited on the inspection surface Wa to form a dark-color defect Wc1 thereon, as shown in FIG. 17A, a color image taken by the imaging unit 3 has a portion other than the dark-color defect Wc1 indicated in blue color B, as shown in FIG. 17B.

In a monochrome image taken by the CCD 21a for red color, the image as a whole is indicated in dark color, and the dark-color defect Wc1 is indicated in even darker color, as shown in FIG. 18A. Accordingly, the brightness distribution in a section taken along line X-X of FIG. 18A is such that the brightness is low over the entire range, and is at an even lower level in a portion corresponding to the dark-color defect Wc1, as shown in FIG. 18D. In the red-color wavelength range, therefore, the specular reflection amount is small, and the diffuse reflection amount is extremely small.

In a monochrome image taken by the CCD 21b for blue color, the image as a whole is indicated in light color, and the dark-color defect Wc1 is indicated in dark color, as shown in FIG. 18B. Accordingly, the brightness distribution in a section taken along line X-X of FIG. 18B is such that the brightness is high over the entire range, and is at a relatively low level only in a portion corresponding to the dark-color defect Wc1, as shown in FIG. 18E. In the blue-color wavelength range, therefore, the specular reflection amount is large, and the diffuse reflection amount is extremely small.

In a monochrome image taken by the CCD 21c for green color, which is similar to the monochrome image taken by the CCD 21a for red color, the image as a whole is indicated in dark color, and the dark-color defect Wc1 is indicated in even darker color, as shown in FIG. 18C. Accordingly, the brightness distribution in a section taken along line X-X of FIG. 18C is such that the brightness is low over the entire range, and is at an even lower level in a portion corresponding to the dark-color defect Wc1, as shown in FIG. 18F. In the green-color wavelength range, therefore, the specular reflection amount is small, and the diffuse reflection amount is extremely small.

By using the above-indicated results of brightness distribution and referring to the pattern analysis table as shown in FIG. 14, the detected object can be identified as the dark-color defect Wc1.

Figure 19A:
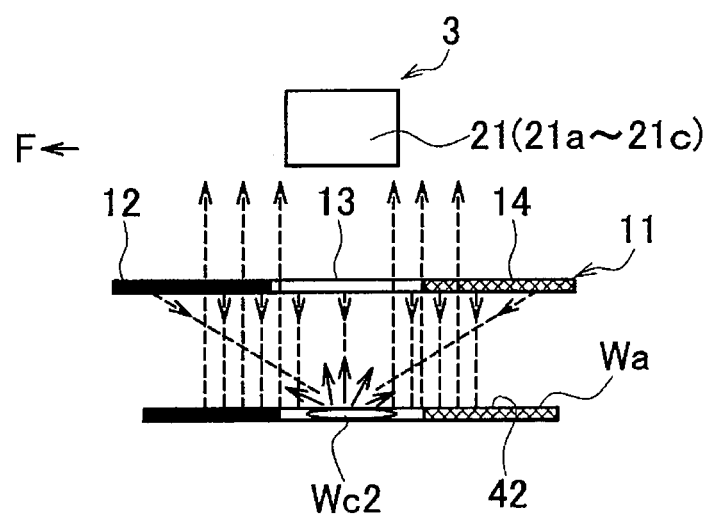
FIG. 19A is a view useful for explaining a method of detecting a color defect (a light-color defect on dark color)
Figure 19B:
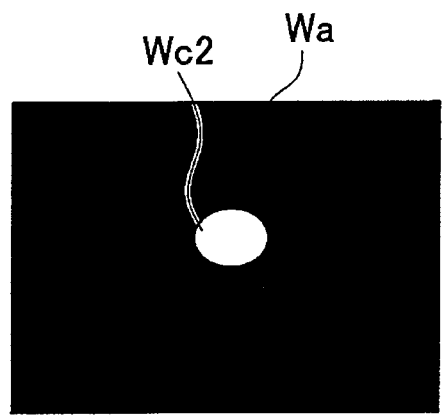
FIG. 19B is a schematic view showing a color image taken by the imaging unit.

When the imaging unit 3 images an inspection surface Wa that is coated with a dark-color (e.g., black) paint, where a dot-like light-color (e.g., white) paint is deposited on the inspection surface Wa to form a light-color defect Wc2 thereon, as shown in FIG. 19A, a color image taken by the imaging unit 3 has a portion other than the light-color defect Wc2 indicated in blue color B, as shown in FIG. 19B.

In a monochrome image taken by the CCD 21a for red color, the image as a whole is indicated in dark color, and the light-color defect Wc2 is indicated in somewhat lighter color than the other portion, as shown in FIG. 20A. Accordingly, the brightness distribution in a section taken along line X-X of FIG. 20A is such that the brightness is low over the entire range, and is at a somewhat higher value in a portion corresponding to the light-color defect Wc2, than that of the other portion, as shown in FIG. 20D). In the red-color wavelength range, therefore, the specular reflection amount is small, and the diffuse reflection amount is medium.

In a monochrome image taken by the CCD 21b for blue color, the image as a whole is indicated in light color, and the light-color defect Wc2 is indicated in even lighter color, as shown in FIG. 20B. Accordingly, the brightness distribution in a section taken along line X-X of FIG. 20B is such that the brightness is high over the entire range, and is at an even higher level in a portion corresponding to the light-color defect Wc2, as shown in FIG. 20E. In the blue-color wavelength range, therefore, the specular reflection amount is large, and the diffuse reflection amount is medium.

In a monochrome image taken by the CCD 21c for green color, which is similar to the monochrome image taken by the CCD 21a for red color, the image as a whole is indicated in dark color, and the light-color defect Wc2 is indicated in somewhat lighter color than the other portion, as shown in FIG. 20C. Accordingly, the brightness distribution in a section taken along line X-X of FIG. 20C is such that the brightness is low over the entire range, and is at a somewhat higher value in a portion corresponding to the light-color defect Wc2, than that of the other portion, as shown in FIG. 20F. In the green-color wavelength range, therefore, the specular reflection amount is small, and the diffuse reflection amount is medium.

By using the above-indicated results of brightness distribution and referring to the pattern analysis table as shown in FIG. 14, the detected object can be identified as the light-color defect Wc2.

Figure 21A:
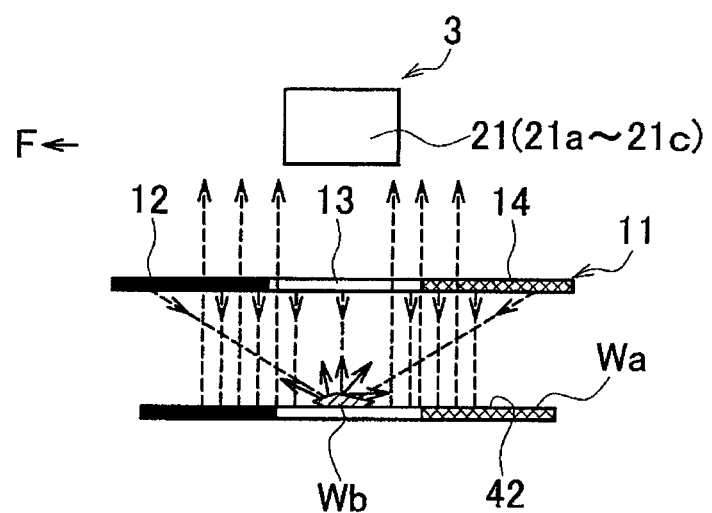
FIG. 21A is a view useful for explaining a method of detecting a foreign matter (such as dust, dirt, or a residue)
Figure 21B:
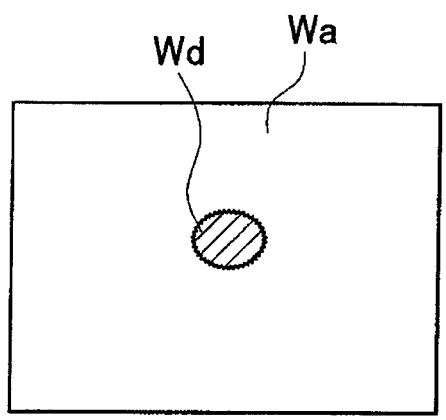
FIG. 21B is a schematic view showing a color image taken by the imaging unit.

When the imaging unit 3 images an inspection surface Wa on which a foreign matter Wd, such as dust, dirt, or a residue, is deposited, as shown in FIG. 21A, a color image taken by the imaging unit 3 has a portion other than the foreign matter Wd indicated in blue color B, as shown in FIG. 21B.

In a monochrome image taken by the CCD 21a for red color, the image as a whole is indicated in dark color, and the foreign matter Wd is indicated in even darker color than the other portion, as shown in FIG. 22A. Accordingly, the brightness distribution in a section taken along line X-X of FIG. 22A is such that the brightness is low over the entire range, and is at an even lower value in a portion corresponding to the foreign matter Wd, than that of the other portion, as shown in FIG. 22D. In the red-color wavelength range, therefore, the specular reflection amount is small, and the diffuse reflection amount is small.

In a monochrome image taken by the CCD 21b for blue color, the image as a whole is indicated in light color, and the foreign matter Wd is indicated in dark color, as shown in FIG. 22B. Accordingly, the brightness distribution in a section taken along line X-X of FIG. 22B is such that the brightness is high over the entire range, and is at a low level in a portion corresponding to the foreign matter Wd, as shown in FIG. 22E. In the blue-color wavelength range, therefore, the specular reflection amount is small, and the diffuse reflection amount is extremely small.

In a monochrome image taken by the CCD 21c for green color, which is similar to the monochrome image taken by the CCD 21a for red color, the image as a whole is indicated in dark color, and the foreign matter Wd is indicated in even darker color than the other portion, as shown in FIG. 22C. Accordingly, the brightness distribution in a section taken along line X-X of FIG. 22C is such that the brightness is low over the entire range, and is at an even lower value in a portion corresponding to the foreign matter Wd, than that of the other portion, as shown in FIG. 22F. In the green-color wavelength range, therefore, the specular reflection amount is small, and the diffuse reflection amount is small.

By using the above-indicated results of brightness distribution and referring to the pattern analysis table as shown in FIG. 14, the detected object can be identified as the foreign matter Wd.

Figure 23A:
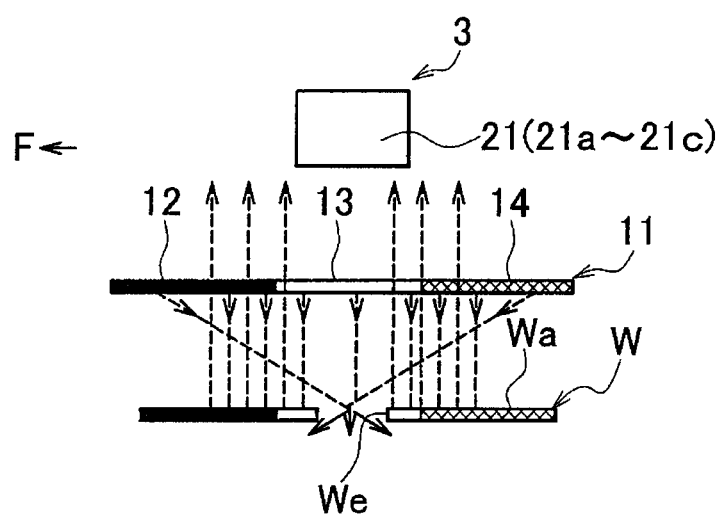
FIG. 23A is a view useful for explaining a method of detecting a shape or design feature (such as a hole, edge, or a step) of the inspection surface.
Figure 23B:
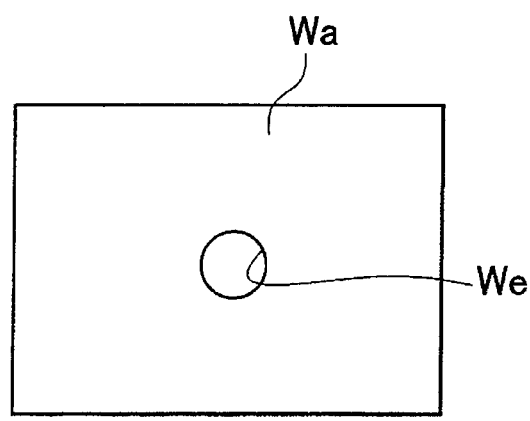
FIG. 23B is a schematic view showing a color image taken by the imaging unit.
Figure 25:
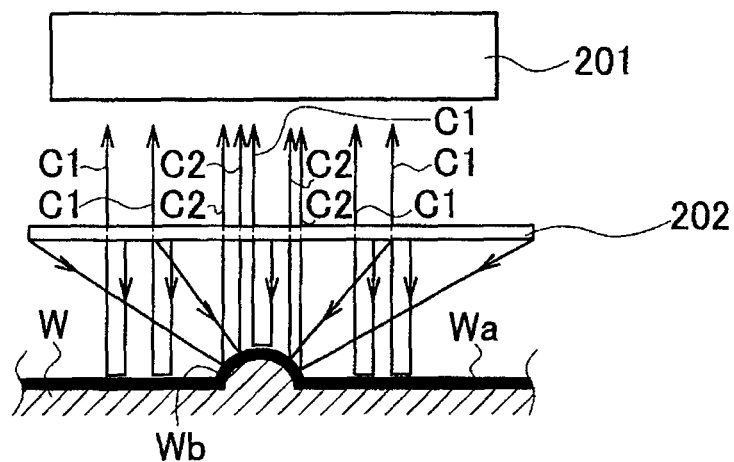
FIG. 25 is a view explaining the case where an area camera and a relatively large illuminator are used.
Figure 26:
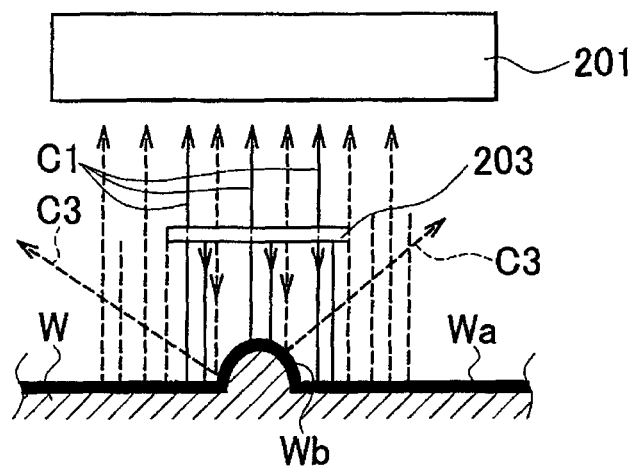
FIG. 26 is a view explaining the case where an area camera and a relatively small illuminator are used.
Figure 27A:
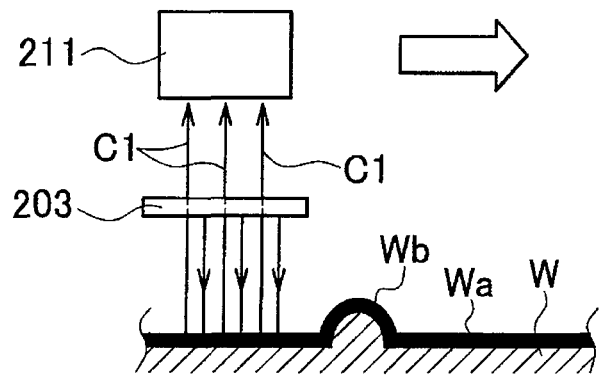
FIG. 27A through FIG. 27C are views explaining the case where a line camera and a relatively small illuminator are used.
Figure 27B:
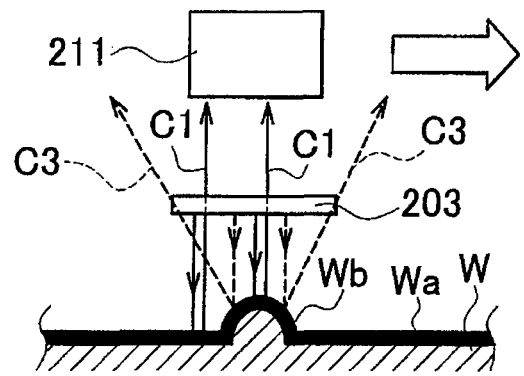
Figure 27C:
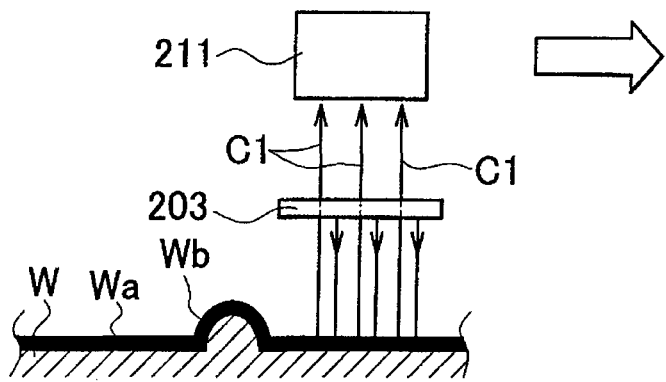
Figure 28:
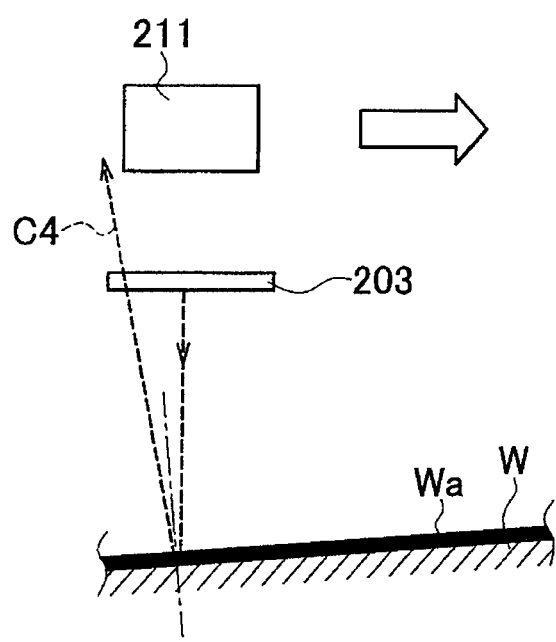
FIG. 28 is a view explaining the related art.

When the imaging unit 3 images an inspection surface Wa in which a hole We used for mounting of a part is formed, for example, as shown in FIG. 23A, a color image taken by the imaging unit 3 has a portion other than the hole We indicated in blue color B, as shown in FIG. 23B.

In a monochrome image taken by the CCD 21a for red color, the image as a whole is indicated in dark color, and the hole We is indicated in black, as shown in FIG. 24A. Accordingly, the brightness distribution in a section taken along line X-X of FIG. 24A is such that the brightness is low over the entire range, and is equal to zero in a portion corresponding to the hole We, as shown in FIG. 24D. In the red-color wavelength range, therefore, the specular reflection amount is extremely small, and the diffuse reflection amount is also extremely small.

In a monochrome image taken by the CCD 21b for blue color, a portion of the image other than the hole We is indicated in light color, and the hole We is indicated in black, as shown in FIG. 24B. Accordingly, the brightness distribution in a section taken along line X-X of FIG. 24B is such that the brightness is high over the entire range, and is equal to zero in a portion corresponding to the hole We, as shown in FIG. 24E. In the blue-color wavelength range, too, the specular reflection amount is extremely small, and the diffuse reflection amount is also extremely small.

In a monochrome image taken by the CCD 21c for green color, which is similar to the monochrome image taken by the CCD 21a for red color, the image as a whole is indicated in dark color, and the hole We is indicated in black, as shown in FIG. 24C. Accordingly, the brightness distribution in a section taken along line X-X of FIG. 24C is such that the brightness is low over the entire range, and is equal to zero in a portion corresponding to the hole We, as shown in FIG. 24F. In the green-color wavelength range, therefore, the specular reflection amount is extremely small, and the diffuse reflection amount is also extremely small.

By using the above-indicated results of brightness distribution and referring to the pattern analysis table as shown in FIG. 14, the detected object can be identified as the hole We. While the hole We is taken as an example of design feature in the embodiment as described above, other design features, such as an edge and a step, may be identified in a similar manner.

According to the embodiment as described above, the image processing means 33 of the control unit 4 identifies a detected object, based on the specular reflection amount and diffuse reflection amount for each wavelength range of reflected light imaged by the imaging unit 3. The specular reflection amount for each wavelength range of reflected light varies with the surface state or shape and the specular reflectance, and the diffusion reflection amount varies with the diffusion reflectance that is influenced by a color, or the like, of the inspection surface. Accordingly, the detected object can be easily identified by analyzing the pattern of specular reflection amounts and diffuse reflection amounts for respective wavelength ranges.

While some embodiments of the invention have been illustrated above, it is to be understood that the invention is not limited to details of the illustrated embodiments, but may be embodied with various changes, modifications or improvements, which may occur to those skilled in the art, without departing from the scope of the invention.

What is claimed is:

1. A surface inspection apparatus, comprising:
an irradiating unit that includes first, second, and third light sources which respectively emit first, second, and third illumination light beams having different wavelength ranges, and irradiates an inspection surface as a surface of a body to be inspected with illumination light beams, in a condition where the first, second, and third light sources are located adjacent to each other and arranged in a given order along the inspection surface;
an imaging unit that images reflected light when the first, second, and third illumination light beams are reflected by the inspection surface, so as to obtain a plurality of items of image data corresponding to the respective wavelength ranges; and
a control unit that detects a detection object on the inspection surface, based on said plurality of items of image data corresponding to the respective wavelength ranges which are obtained by the imaging unit;
wherein the second light source is located between the first light source and the third light source;
wherein the first illumination light beam includes red visible light, the second illumination light beam includes blue visible light and the third illumination light beam includes green visible light;
wherein the irradiating unit further includes a first intermediate light source placed between the first light source and the second light source and a second intermediate light source placed between the second light source and the third light source;
wherein the first intermediate light source is configured to emit a fourth illumination light beam including wavelength ranges of the first and second illumination light beams, and the second intermediate light source is configured to emit a fifth illumination light beam including wavelength ranges of the second and third illumination light beams;
wherein the first, second, and third light sources include a first plurality, a second plurality, and a third plurality of light emitters, respectively, each light emitter of the first plurality of light emitters having the same wavelength range, each light emitter of the second plurality of light emitters having the same wavelength range, and each light emitter of the third plurality of light emitters having the same wavelength range; and wherein the first intermediate light source includes light emitters from the first plurality of light emitters and the second plurality of light emitters arranged in an alternating manner; and the second intermediate light source includes light emitters from both the second plurality of light emitters and the third plurality of light emitters, arranged in an alternating manner.

2. A surface inspection apparatus, comprising:

an irradiating unit that includes first, second, and third light sources which respectively emit first, second, and third illumination light beams having different wavelength ranges, and irradiates an inspection surface as a surface of a body to be inspected with illumination light beams, in a condition where the first, second, and third light sources are located adjacent to each other and arranged in a given order along the inspection surface;

an imaging unit that images reflected light when the first, second, and third illumination light beams are reflected by the inspection surface, so as to obtain a plurality of items of image data corresponding to the respective wavelength ranges; and a control unit that detects a detection object on the inspection surface, based on said plurality of items of image data corresponding to the respective wavelength ranges which are obtained by the imaging unit;

wherein the second light source is located between the first light source and the third light source;

wherein the first illumination light beam includes red visible light, the second illumination light beam includes blue visible light and the third illumination light beam includes green visible light;

wherein the irradiating unit further includes a diffusion plate, the diffusion plate including first, second, and third single-color light emitting regions each of which allows the first, second, and third illumination light beams, and a first intermediate light emitting region that is provided between the first and second single-color light emitting regions, and a second intermediate light emitting region that is provided between the second and third single-color light emitting regions;

wherein the first intermediate light emitting region is configured to emit a fourth illumination light beam of a color combination obtained by mixing the first and second light beams; and wherein the second intermediate light emitting region is configured to emit a fifth illumination light beam of a color combination obtained by mixing the second and third light beams.

\* \* \* \* \*